United States Patent
Treadwell et al.

(10) Patent No.: US 11,773,046 B2
(45) Date of Patent: Oct. 3, 2023

(54) SOLVOTHERMAL SYNTHESIS OF METAL ALKANOATE AND METAL OXIDE NANOPARTICLES

(71) Applicant: National Technology & Engineering Solutions of Sandia, LLC, Albuquerque, NM (US)

(72) Inventors: LaRico Juan Treadwell, Albuquerque, NM (US); Clare Davis-Wheeler, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 374 days.

(21) Appl. No.: 17/315,497

(22) Filed: May 10, 2021

(65) Prior Publication Data
US 2021/0347719 A1 Nov. 11, 2021

Related U.S. Application Data

(60) Provisional application No. 63/022,725, filed on May 11, 2020.

(51) Int. Cl.
| | | |
|---|---|---|
| *C07C 51/41* | (2006.01) | |
| *B01J 6/00* | (2006.01) | |
| *C01F 17/229* | (2020.01) | |
| *B01J 19/12* | (2006.01) | |

(Continued)

(52) U.S. Cl.
CPC .............. *C07C 51/41* (2013.01); *B01J 6/001* (2013.01); *B01J 19/126* (2013.01); *C01F 17/229* (2020.01); *C07C 51/412* (2013.01); *C07C 51/43* (2013.01); *B01J 2219/00141* (2013.01); *B82Y 40/00* (2013.01); *C01P 2004/64* (2013.01)

(58) Field of Classification Search
None
See application file for complete search history.

(56) References Cited

U.S. PATENT DOCUMENTS

| | | | | |
|---|---|---|---|---|
| 2006/0211152 A1* | 9/2006 | Peng | ...................... | C01G 53/04 977/963 |
| 2007/0018140 A1* | 1/2007 | Lee | ........................... | B22F 9/24 252/500 |
| 2011/0002872 A1* | 1/2011 | Ohashi | ...................... | B22F 9/30 524/439 |

FOREIGN PATENT DOCUMENTS

WO   WO-2012155931 A1 * 11/2012 ............. B82Y 30/00

OTHER PUBLICATIONS

Binnemans, K. et al., "Lanthanide(III) Dodecanoates: Structure, Thermal Behaviour, and Ion-Size Effects on the Mesomorphism," European Journal of Inorganic Chemistry, 2000, pp. 1429-1436.
(Continued)

*Primary Examiner* — Amy C Bonaparte
(74) *Attorney, Agent, or Firm* — Kevin W. Bieg

(57) ABSTRACT

A facile solvothermal method can be used to synthesize metal alkanoate nanoparticles using a metal nitrate precursor, alcohol/water, and alkanoic acid. The method can produce lanthanide (e.g., La, Ce, Pr, Nd, Sm, Eu, Gd, Tb, Dy, Ho, Er, Tm, or Yb) and transition metal (e.g., Ag, Co, Cu, or Pb) alkanoate nanoparticles (<100 nm) with spherical morphology. These hybrid nanomaterials adopt a lamellar structure consisting of inorganic metal cation layers separated by an alkanoate anion bilayer and exhibit liquid crystalline phases during melting. The metal alkanoate nanoparticles can be calcined to produce metal oxide nanoparticles.

13 Claims, 16 Drawing Sheets

(51) Int. Cl.
    *C07C 51/43*    (2006.01)
    *B82Y 40/00*    (2011.01)

(56) References Cited

OTHER PUBLICATIONS

Binnemans, K., "Lanthanide-Based Luminescent Hybrid Materials," Chemical Reviews, 2009, vol. 109, pp. 4283-4374.

Goossens, K. et al., "Ionic Liquid Crystals: Versatile Materials," Chemical Reviews, 2016, vol. 116, pp. 4643-4807.

Misra, S. N. et al., "Organic Salts of Lanthanide Elements—II," Journal of Inorganic Nuclear Chemistry, 1963, vol. 25, pp. 201-203.

Mehrotra, K.N. et al., "Physico-Chemical Studies on Samarium Soaps in Solid State," Monatshefte für Chemie Chemical Monthly, 1989, vol. 120, pp. 1063-1068.

Karmaoui, M. et al., "Lanthanide-Based Lamellar Nanohybrids: Synthesis, Structural Characterization, and Optical Properties," Chemistry of Materials, 2006, vol. 18, pp. 4493-4499.

Martinez-Casado, F. J. et al., "Lead(II) Soaps: Crystal Structures, Polymorphism, and Solid and Liquid Mesophases," Physical Chemistry Chemical Physics, 2017, vol. 19, 17009-17018.

Ramos Riesco, M. et al., "Study of the Polymorphism in Copper(II) Decanoate through Its Phase Diagram with Decanoic Acid, and Texture of the Columnar Thermotropic Liquid Crystal Developable Domains in This and Similar Systems," Crystal Growth and Design, 2015, vol. 15, pp. 497-509.

Klimusheva, G. et al., "Versatile Nonlinear-Optical Materials Based on Mesomorphic Metal Alkanoates: Design, Properties, and Applications," Liquid Crystals Review, 2015, vol. 3, pp. 28-57.

Binnemans, K. et al., "Structure and Mesomorphism of Silver Alkanoates," Chemistry of Materials, 2004, vol. 16, pp. 2021-2027.

Binnemans, K. et al., "Optical Properties of Vitrified Rare-Earth Soaps," Physical Chemistry Chemical Physics, 2001, vol. 3, pp. 4796-4799.

Nguyen, T-D. et al., "Shape- and Size-Controlled Synthesis of Monoclinic ErOOH and Cubic $Er_2O_3$ from Micro- to Nanostructures and Their Upconversion Luminescence," ACS Nano, 2010, vol. 4, pp. 2263-2273.

* cited by examiner

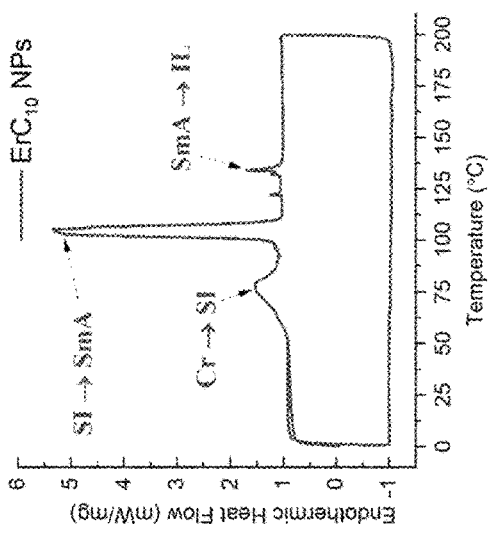
FIG. 14A
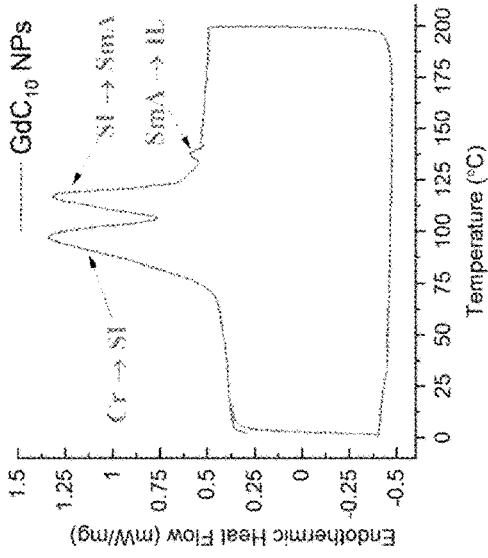
FIG. 14B
FIG. 14C
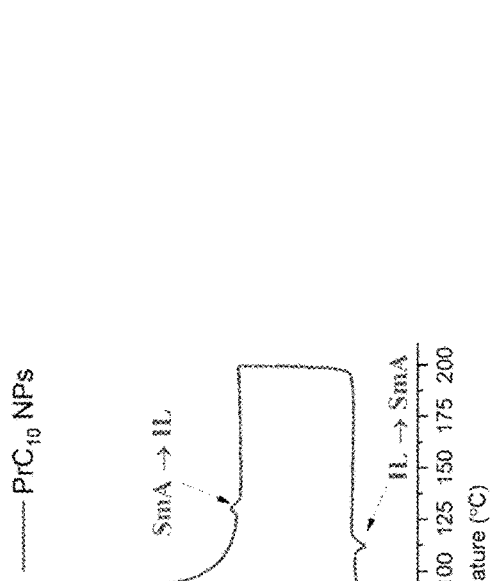
FIG. 14D
FIG. 14E

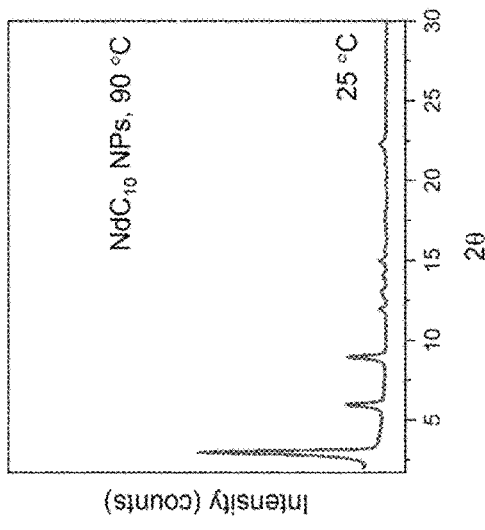
FIG. 15A
FIG. 15B
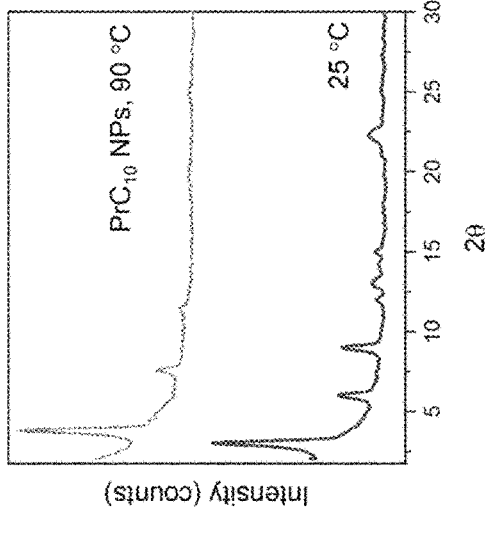
FIG. 15C
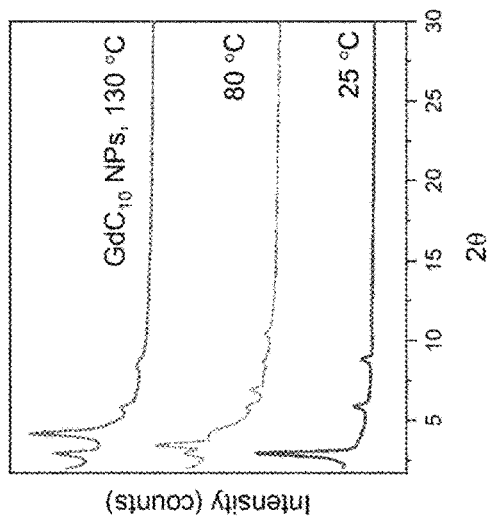
FIG. 15D
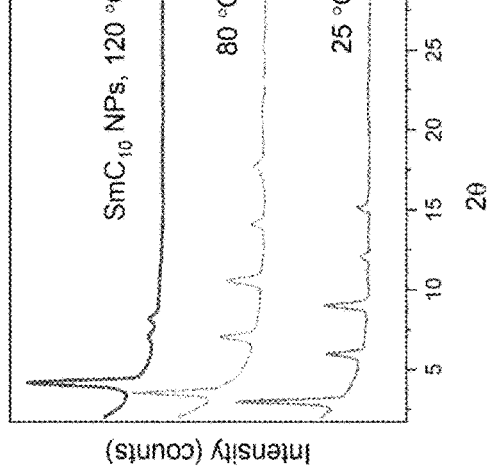
FIG. 15E

SOLVOTHERMAL SYNTHESIS OF METAL ALKANOATE AND METAL OXIDE NANOPARTICLES

CROSS-REFERENCE TO RELATED APPLICATION

This application claims the benefit of U.S. Provisional Application No. 63/022,725, filed May 11, 2020, which is incorporated herein by reference.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to nanoparticles and, in particular, to the solvothermal synthesis of metal alkanoate and metal oxide nanoparticles.

BACKGROUND OF THE INVENTION

In recent years, lanthanide-based organic-inorganic hybrid materials have attracted significant interest as substitutes for conventional lanthanide oxides in nanoreactors, polymer stabilizers, heterogeneous catalysts, photosensitizers, and OLEDs. See K. Binnemans et al., *Eur. J. Inorg. Chem.* 2000(7), 1429 (2000); K. Binnemans, *Chem. Rev.* 109, 4283 (2009); and K. Goossens et al., *Chem. Rev.* 116(8), 4643 (2016). This wide variety of applications is a direct consequence of their lamellar structural motif, which facilitates interactions between the organic and inorganic components. Lanthanide alkanoates (or soaps) are lamellar hybrids that form 2D coordination polymers in which inorganic layers of 2D $Ln^{3+}$ polyhedra are coordinated to organic layers of intercalated alkanoate anions. See S. N. Misra et al., *J. Inorg. Nucl. Chem.* 25(2), 201 (1963); and K. N. Mehrotra et al., *Monatsh. Chem.* 120(12), 1063 (1989). This structural build has directly led to the enhancement of mechanical properties, better processability, increased thermal stability, and improved optical activity over materials with conventional lanthanide compounds. See K. Binnemans, *Chem. Rev.* 109, 4283 (2009). For example, the amphiphilic nature of lanthanide alkanoates allows them to be homogeneously incorporated into polymer matrices for fabrication of versatile composite materials. See E. F. Marques et al., *J. Chem. Soc., Faraday Trans.* 94, 1729 (1998). As a result, polymer composites utilizing lanthanide alkanoates have shown superior tensile strength, better thermal stability, and increased luminescence output. See M Karmaoui et al., *Chem. Mater.* 18(18), 4493 (2006). Cerium alkanoates area widely used in paints and fuels due to their intrinsic oxidizing properties and ability to form coordination compounds with organic ligands. Compared to conventional cerium oxide materials, cerium alkanoates' higher reactivity and decreased electrochemical corrosion properties result in significant improvements to combustion efficiency and the reduction of particulate emissions when added to diesel and other fuels. See P. Ducros, *J. Less Common Met.* 111(1), 37 (1985).

The organic component of hybrid materials such as lanthanide alkanoates provides a major pathway to enhanced lanthanide luminescence for specific targeted applications such as solid-state lighting, radiation converters and sensors, lasing media, optical amplifiers, and biomedical analysis and imaging. See J.-C. G. Bunzli, *Chem. Rev.* 110, 2729 (2010); and S. Liu et al., *Chem. Eng. J.* 380, 122618 (2020). Organic-inorganic hybrid materials often utilize the "antenna effect" between $Ln^{3+}$ and sensitizing metal ligand complexes, in which energy absorbed by organic receptors is transferred to $Ln^{3+}$ excited states and produces strong, sharp emissions. See J. C. G. Bunzli and C. Piguet, *Chem. Soc. Rev.* 34, 1048 (2005). Karmaoui et al. observed significantly enhanced luminescence efficiency in layered lanthanide complexes containing intercalated benzoate ions, which was attributed to transfer of excitation from the benzoate phenyl rings to the $Ln^{3+}$ centers. See M. Karmaoui et al., *Chem. Mater.* 18(18), 4493 (2006).

The structural anisotropy of the lanthanide alkanoates' lamellar motif gives rise to unusual thermal behavior, which can be used to generate useful phases such as liquid crystals and vitrified glass. See R. W. Corkery and J. P. D. Martin, *J. Lumin.* 82(1), 1 (1999); and K. Binnemans et al., *Phys. Chem. Chem. Phys.* 3, 10 (2001). Increasing temperatures can induce the formation of thermotropic liquid crystalline phases, which have been observed during the melting of lighter lanthanides (Ln=La, Ce, Pr, and Nd) and transition metal alkanoates, such as Pb, Cu, Co, and Ag. See M. Karmaoui et al., *Chem. Mater.* 18, 4493 (2006); F. J. Martinez-Casado et al., *Phys. Chem. Chem. Phys.* 19, 17009 (2017); M. Ramos Riesco et al., *Cryst. Growth Des.* 15(1), 497 (2015); G. Klimusheva et al., *Liq. Cryst.* Rev. 3(1), 28 (2015); and K. Binnemans et al., *Chem. Mater.* 16(10), 2021 (2004). According to a recent report by Garbovskiy et al., the liquid crystals of long-chain cobalt alkanoates $CoC_n$ (n=8, 10, 12) exhibited third-order optical nonlinearity in the presence of an applied electromagnetic field. See Y. A. Garbovskiy et al., *Liq. Cryst.* 34, 599 (2007). Once fully melted, the ionic liquid phase can be easily quenched to form optical glasses and composites that produce nonlinear optical responses. See K. Binnemans et al., *Phys. Chem. Chem. Phys.* 3, 10 (2001); and F. J. Martinez-Casado et al., *Phys. Chem. Chem. Phys.* 19, 17009 (2017).

With respect to luminescence, the layered environment and long chain of lanthanide alkanoates give rise to unique optical properties but are described by only a small number of reports. As synthesized, room temperature Ln alkanoates are generally regarded as optically inactive due to luminescence quenching by hydroxyl, crystal water, or carboxylate groups, which provide pathways for non-radiative relaxation. See H. Li et al., *J. Phys Chem. B* 109, 21669 (2005); K. Ren et al., *Opt. Mater.* 105, 109884 (2020); and B. Barja et al., *Morgan. Chim. Acta* 346, 187 (2003). For example, Li et al. observed significantly reduced emission intensities in long-chain europium alkanoates ($EuC_{16}$) compared to $Eu(NO_3)_3$ and the absence of the characteristic intense red luminescence under UV irradiation. See H. Li et al., *J. Phys. Chem. B* 109, 21669 (2005). They attributed this to quenching of $Eu^{3+}$ excited states by non-radiative relaxation to closely-lying $\pi^*$ orbitals of the alkanoate carboxylate groups. While various treatments such as calcination to remove quenching species have been explored, the most promising methods for improving luminescence in lanthanide alkanoates take advantage of their mesomorphic behavior. Binnemans et al. found that vitrification via fast cooling of $LnC_{18}$ (Ln=Nd, Sm, Eu, Gd, Dy, Ho, Er) from the ionic liquid phase produced optical glasses with photoluminescence intensities comparable to those of lanthanide oxide glasses. See K. Binnemans et al., *Phys. Chem. Chem. Phys.* 3, 10 (2001). Further advances in the design of mesomorphic glasses have generated increased research in the field of photonic and optoelectronic materials based on mesomorphic metal alkanoates. See G. Klimusheva et al., *Liq. Cryst. Rev.* 3, 28 (2015).

Due to the importance of the structural motif and elements present, several synthetic routes have been published for the production of highly crystalline bulk lanthanide alkanoates. The majority of these routes utilized a metathesis reaction between the sodium alkanoate $Na(C_nH_{2n+1}COO; n=4-22)$ and lanthanide nitrate precursors in aqueous/ethanol solution, followed by recrystallization from pentanol. See L. Jongen et al., *Liq. Cryst.* 28(6), 819 (2001); and K. Binnemans and C. Gorller-Walrand, *Chem. Rev.* 102(6), 2303 (2002). An alternate route reacted lanthanide(III) isopropoxide precursors with the desired alkanoic acid in a 1:3 molar ratio in anhydrous benzene, followed by refluxing for 4 hours. Products were isolated by low-pressure distillation at room temperature. See M. Hasan et al., *J. Prakt. Chem.* 4, 313 (1968).

Though far less common than their bulk counterparts, organic-inorganic hybrid materials on the nanoscale have been found to offer significantly enhanced properties and versatility. Various studies on lamellar hybrid nanomaterials have reported enhanced catalytic activity for photooxidation of organic pollutants, increased optical emission, and greater flexibility for dispersion into polymer matrices. See K. Binnemans, *Chem. Rev.* 109, 4283 (2009). Despite these potential advantages, very few synthetic routes to nanoscale materials can be found in the literature. Karmaoui et al. described a non-aqueous solvothermal route to ordered nanocrystalline lanthanide hybrids (Ln=Gd, Sm, Eu) that utilized lanthanide isopropoxide precursors dissolved in benzyl alcohol. See M. Karmaoui et al., *Chem. Mater.* 18(18), 4493 (2006). The products adopted a nanoplatelet morphology that could be tuned by varying reaction temperature, and exhibited enhanced thermal stability and increased optical emissions compared to their bulk counterparts. Di et al. modified the nonaqueous synthetic route to generate lanthanide phenylphosphonate lamellar nanohybrids (Ln=Y, La) that displayed significantly enhanced photoluminescence over bulk materials. See W. Di et al., *J. Phys. Chem. C* 114(14), 6290 (2010).

However, a need remains for a facile, reproducible synthetic route for nanoscale lamellar hybrid materials that eliminates the parasitic variables found in current methods. For example, insufficient control of reaction mixture pH and solubility often results in phase impurities or low crystallinity in products of the metathestic method. See K. Binnemans and C. Gorller-Walrand, *Chem. Rev.* 102(6), 2303 (2002). These products may also contain hydroxyl groups, which can cause significant luminescence quenching. See W. Di et al., *J. Phys. Chem. C* 114(14), 6290 (2010). The non-aqueous used for nanoscale materials is a complex process carried out in an inert atmosphere over a long (48 hours) reaction time and involves the safety risk of heating stainless steel autoclaves at high temperatures (250-300° C.). See L. Saviot et al., *J. Phys. Chem. C* 121(3), 1990 (2017).

SUMMARY OF THE INVENTION

The present invention is directed toward a facile "one-pot" solvothermal synthesis of shape-controlled lanthanide and transition metal alkanoate and lanthanide and transition metal oxide nanoparticles. A method to synthesize metal alkanoate nanoparticles comprises the steps of dissolving a metal nitrate precursor in water to provide an aqueous metal precursor solution, dissolving an alkanoic acid (RCOOH, where R is an alkyl chain) in an alcohol to provide an alkanoate solution, mixing the aqueous metal precursor solution with the alkanoate solution to provide a mixed solution, heating the mixed solution to a reaction temperature to form metal alkanoate precipitate, and dispersing the metal alkanoate precipitate to provide metal alkanoate nanoparticles. For example, the metal can comprise a lanthanide, such as La, Ce, Pr, Nd, Sm, Eu, Gd, Tb, Dy, Ho, Er, Tm, or Yb. For example, the metal can comprise a transition metal, such as Ag, Co, Cu, or Pb. The alcohol can comprise a short-chain alcohol, such as methanol, ethanol, propanol, or butanol. Preferably, the heating step comprises microwave heating to a reaction temperature of greater than 80° C. for transition metal alkanoates and greater than 120° C. for lanthanide alkanoates. The resulting metal alkanoate can comprise a di- or tri-valent metal cation coordinated to the carboxy group of an alkanoate anion with 4 to 22 carbon atoms in the alkyl chain. The method can further comprise calcining the metal alkanoate nanoparticles at a calcination temperature of greater than 400° C. to provide metal oxide nanoparticles.

BRIEF DESCRIPTION OF THE DRAWINGS

The detailed description will refer to the following drawings, wherein like elements are referred to by like numbers.

FIGS. 10A-D show photoluminescence emission spectra for: FIG. 10A, Er; FIG. 10B, Sm; FIGS. 10C-D, $EuC_{10}$ NPs, which all have bright emissions in the visible range. Transition identities and excitation wavelengths are noted on each spectrum.

FIGS. 11A-D show photoluminescence emission spectra and transitions for: FIGS. 11A-B, Pr; FIG. 11C, Nd; and FIG. 11D, $GdC_{10}$ NPs. Emission bands for $GdC_{10}$ NPs in FIG. 11D are not labeled with transitions, since the emissions most likely originated from excited state deactivation via electron recombination rather than relaxation through radiative emission.

FIG. 12A is a CIE diagram for excitation wavelengths from 260-285 nm (see FIGS. 10 and 11 for corresponding PL spectra). FIG. 12B is a CIE diagram for excitation wavelengths corresponding visible PL by colloidal suspensions of $LnC_{10}$ NPs under long-wave UV irradiation (PL emission spectra $\lambda_{ex}$=395 nm). These calculated CIE coordinates agree with visible PL observed from colloidal dispersions of $LnC_{10}$ NPs under long-wave UV irradiation (Ln=Nd, Sm, Eu, Gd, Er) with the exception of $PrC_{10}$ NPs, which did not visibly luminescence.

FIGS. 14A-E are DSC traces for $LnC_{10}$ NPs, including transitions between solid crystalline (Cr), solid intermediate rotator (SI), liquid crystalline smectic A (SmA), and isotropic liquid (IL) phases for: FIG. 14A, $SmC_{10}$ NPs; FIG. 14B, $GdC_{10}$ NPs; FIG. 14C, $ErC_{10}$ NPs; FIG. 14D, $NdC_{10}$ NPs; and FIG. 14E, $PrC_{10}$ NPs.

FIGS. 15A-E are HT-PXRD spectra of $LnC_{10}$ NPs mesophase(s) compared to room temperature diffraction spectra for: FIG. 15A, $PrC_{10}$; FIG. 15B, $NdC_{10}$; FIG. 15C, $SmC_{10}$; FIG. 15D, $GdC_{10}$; and FIG. 15E, $ErC_{10}$.

FIGS. 16A and 16B show changes in $d_{max}$ values vs. temperature over solid crystalline, intermediate, and Smectic A and C liquid crystalline phases for: FIG. 16A, $PrC_{10}$ NPs, and FIG. 16B, $ErC_{10}$ NPs. Values were calculated from HT-PXRD patterns.

DETAILED DESCRIPTION OF THE INVENTION

Figure 1:
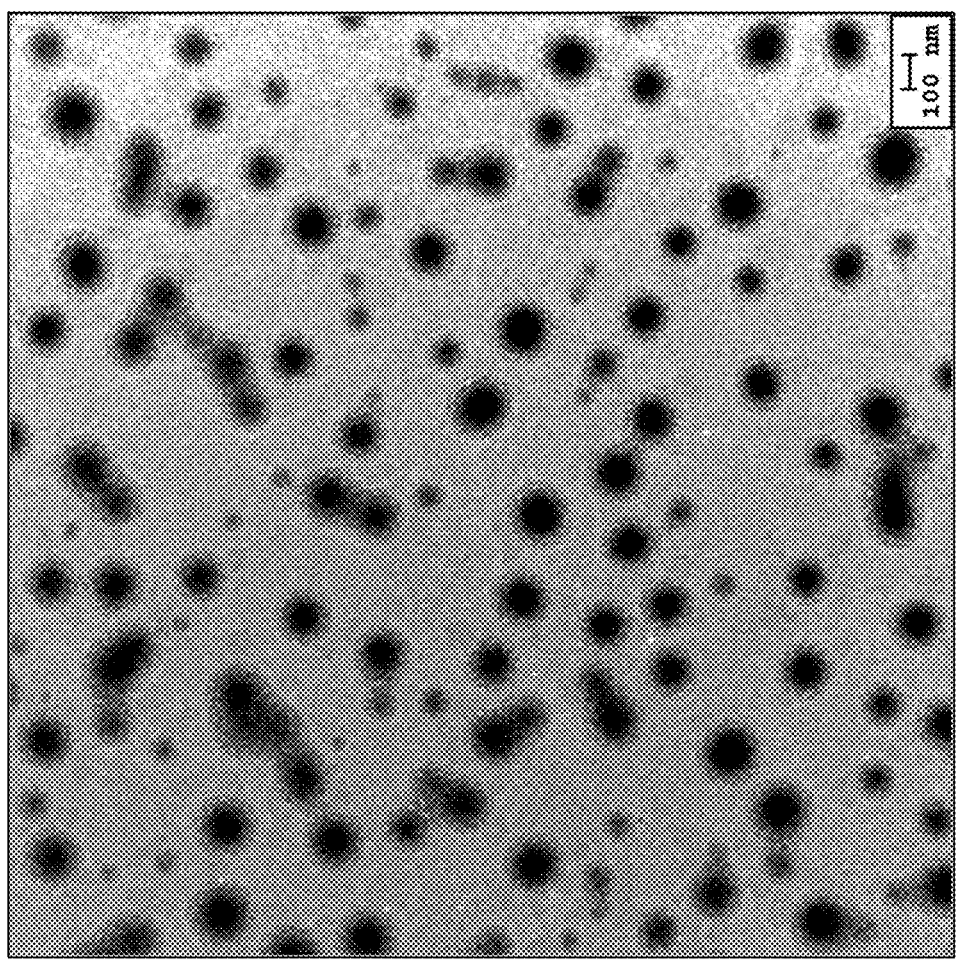
FIG. 1 is a transmission electron microscopy (TEM) image of the produce obtained from the solvothermal microwave synthesis of decanoic acid with a samarium nitrate precursor.

The present invention is directed to a facile "one-pot" microwave (MWV) route as an alternative to the conventional synthesis methods for producing nanoscale lanthanide or transition-metal alkanoate lamellar hybrid materials. MWV methods offer the ability to reproducibly synthesize high-quality nanoparticles while minimizing safety risks and eliminating the influence of many parasitic variables associated with conventional heating techniques by direct interaction with active species in MWV-transparent reaction vessels. See C. Davis-Wheeler Chin et al., *MRS Commun.* 8, 71 (2018); M. Baghbanzadeh et al., *Angew. Chem. Int. Ed.* 50(48), 11312 (2011); J. Robinson et al., *Phys. Chem. Chem. Phys.* 12, 4750 (2010); and T. Rostamzadeh et al., *Chem-NanoMat* 5, 1373 (2019).

As an example, the solvothermal method of the present invention can be used for the MWV synthesis of shape-controlled lanthanide decanoate nanoparticles ($LnC_{10}$ NPs, Ln=Pr, Nd, Sm, Eu, Gd, Er). The exemplary method uses low-cost, environmentally friendly reagents to produce $LnC_{10}$ nanospheres in high yield and can be easily scaled to produce multi-gram quantities. As described below, characterization via transmission electron microscopy (TEM), powder X-ray diffraction (PXRD), Fourier transform infrared spectroscopy (FTIR), and thermal gravimetric analysis (TGA) was conducted to explore the morphology, composition, and structure of the $LnC_{10}$ NPs. Detailed thermal analysis via differential scanning calorimetry (DSC) and high temperature powder X-ray diffraction (HT-PXRD) revealed the formation of liquid crystalline phases in all products. Examination of optical properties was conducted via UV-visible and steady-state photoluminescence spectroscopy, and revealed strong luminescence emissions in the visible region by the various $LnC_{10}$ NPs. This synthesis method can be easily extended to include other lanthanide (e.g., La, Ce, Pr, Nd, Sm, Eu, Gd, Tb, Dy, Ho, Er, Tm, or Yb), transition metals (e.g., Ag, Co, Cu, Pb), and alkali metals that can form stable nitrate salts, as well as metal alkanoates, for example, $Ln(C_nH_{2n+1}COO)_x$ (abbreviation: $L_nC_{n+1}$) where x can be 2 or 3, and n can be 4 to 22 carbons in the alkyl chain. Further, adjusting the reaction conditions can allow tunability of thermal and optical properties through control of product composition and motif.

Synthesis of Lanthanide Decanoate Nanoparticles Via Microwave Heating

To demonstrate the utility of this invention for producing lamellar metal alkanoate nanohybrid materials, solvothermal synthesis of lanthanide decanoate nanoparticles ($LnC_{10}$ NPs) was performed via MWV irradiation of commercial $Ln(NO_3)_3$ precursors and decanoic acid ($HC_{10}$) in a water/ethanol solvent mixture. The reaction between the lanthanide nitrate precursor and decanoate acid produces $LnC_{10}$ as represented by Equation (1):

$$Ln(NO_3)_3 + 3C_9H_{19}COOH \xrightarrow{\Delta} Ln(C_9H_{19}COO)_3 + 3HNO_3 \quad (1)$$

wherein the unstable $HNO_3$ product quickly decomposes into water vapor and $NO_2$ gas. A similar synthetic procedure using conventional heating produced $Ln_2O_3$ oxides nanoparticles. See T. D. Nguyen et al., *ACS Nano* 4, 2263 (2010).

In a standard synthesis method, 0.36 mmol of a lanthanide nitrate precursor $Ln(NO_3)_3 \cdot xH_2O$ (i.e., praseodymium(III) nitrate hexahydrate ($Pr(NO_3)_3 \cdot 6H_2O$), neodymium(III) nitrate hexahydrate ($Nd(NO_3)_3 \cdot 6H_2O$), samarium(III) nitrate hexahydrate ($Sm(NO_3)_3 \cdot 6H_2O$), europium(III) nitrate pentahydrate ($Eu(NO_3)_3 \cdot 5H_2O$), gadolinium(III) nitrate hexahydrate ($Gd(NO_3)_3 \cdot 6H_2O$), or erbium(III) nitrate pentahydrate ($Er(NO_3)_3 \cdot 5H_2O$)) and 10 mL DI $H_2O$ were combined in a 100 mL EasyPrep Plus™ Teflon TFM 1700 reaction vessel lined with a protective sleeve to form an aqueous metal precursor solution. A PTFE-coated rare earth magnetic stir bar was placed in the vessel and the contents were stirred at room temperature for 5 minutes. A decanoic acid solution was prepared by stirring 18 mmol $HC_{10}$ in 30 mL absolute ethanol (EtOH) at 650 rpm for 10 minutes at 70° C. The $HC_{10}$/EtOH solution was then added to the aqueous metal precursor solution and stirred briefly in order to mix the solutions.

After the constituents were added to the vessel, it was placed in a CEM Mars 6 Microwave Reaction System equipped with a single magnetron generator operating at 2.45 GHz and a microprocessor-controlled power output of up to 1800 W. The prepared reaction vessels were heated via MWV irradiation at a maximum power output of 1100 W to 180° C. at a rate of 8° C./minute, held for 5 hours, then allowed to cool to room temperature. The products of the MWV reactions were isolated by centrifugation for 5 minutes at 6000 rpm, after which the clear supernatant was discarded and the precipitate was redispersed in hexane and isopropyl alcohol (IPA), briefly sonicated, and recentrifuged. This washing procedure was repeated three times to yield powders with colors that varied by precursor: blue (Pr), green (Nd), yellow-white (Sm), white (Eu and Gd), and pink (Er). The resultant powders were dried overnight at room temperature and stored for characterization. Yields of each obtained product were as follows: Pr, 64.5%; Nd, 77.2%; Sm, 86.3%; Eu, 82.4%; Gd, 71.3%; and Er, 85.4%.

In order to convert the MWV-synthesized $LnC_{10}$ NPs to the oxide phase, the dried NPs were placed in an alumina crucible and heated in air at 500° C. for 1 h, then allowed to cool to room temperature to provide lanthanide oxide nanoparticles.

Motif and Composition of Microwave Synthesis Products

Transmission electron microscopy (TEM) images were collected to examine the products obtained from the solvothermal microwave reaction of decanoic acid with the various $Ln(NO_3)_3$ precursors (Ln=Pr, Nd, Sm, Gd, Er). All reactions produced nanoparticles with spherical morphology. FIG. 1 shows representative Sm decanoate nanoparticles. Average nanoparticle diameter was determined via analysis of the electron micrographs and was found to decrease as the atomic number of the lanthanide increased, ranging from 96 nm (Pr) to 60 nm (Er). This decrease coincides with the contraction of ionic radius across the lanthanide series.

Figure 2B:
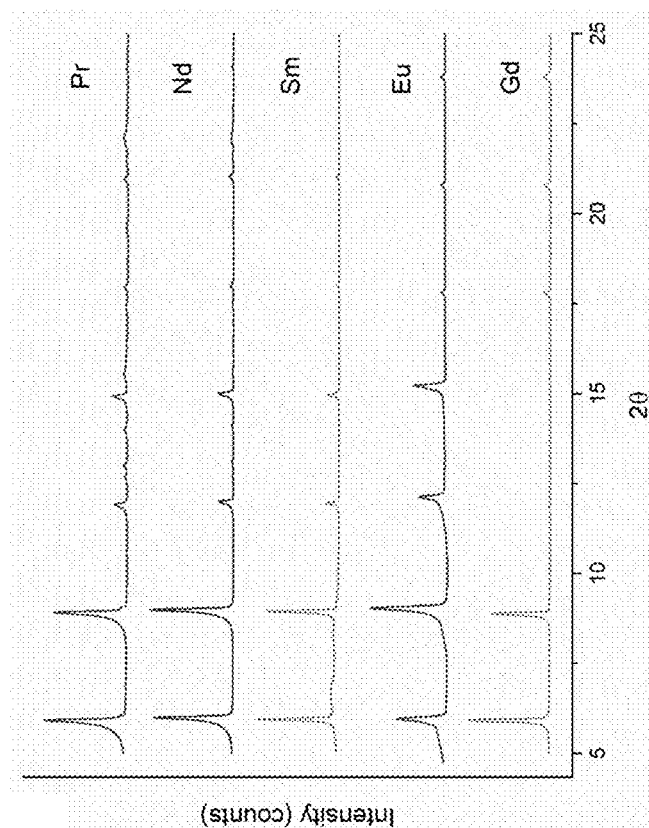
FIG. 2B shows room temperature PXRD patterns of the other MWV products from nitrate precursors, $Ln(NO_3)_3 \cdot xH_2O$ (Ln=Pr, Nd, Sm, Eu, Gd). All diffraction patterns displayed a series of high intensity peaks at low angles, indicating a layered structure.
Figure 2A:
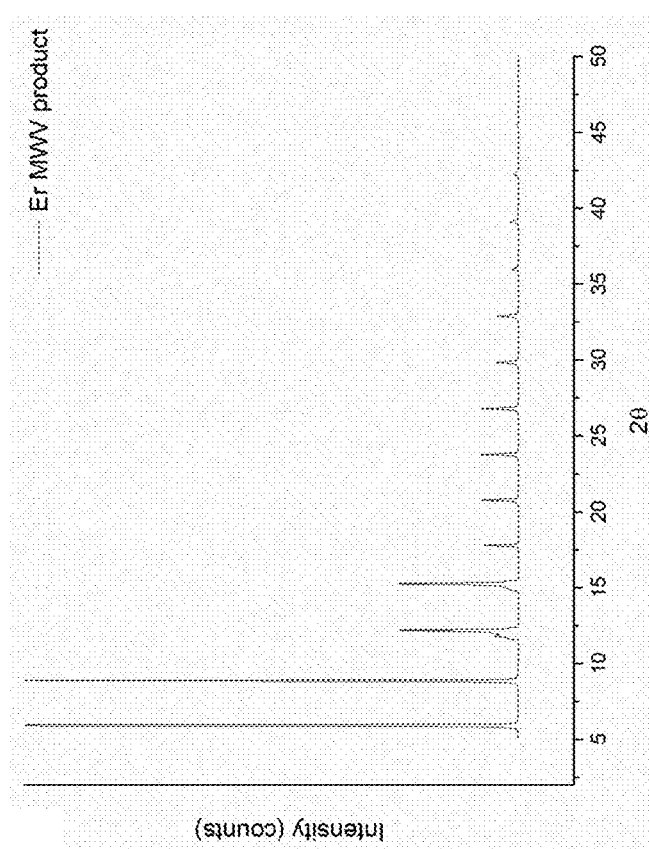
FIG. 2A is a PXRD pattern of the MWV reaction product of $Er(NO_3)_3 \cdot 5H_2O$ and decanoic acid collected at room temperature.

PXRD data were collected on the products isolated from the microwave solvothermal reactions. All diffraction patterns showed a series of high intensity peaks from 5-25° as well as a set of evenly spaced, lower intensity peaks at higher angles, as shown in FIGS. 2A and 2B. Peak position was in good agreement with previously reported lanthanide decanoate PXRD spectra that identified the low-angle diffraction peaks with the organic-inorganic layer, while peaks observed in the high-angle region were attributed to diffraction by the planes of $Ln^{3+}$ atoms. See M. Ramos Riesco et al., *Cryst. Growth Des.* 15, 497 (2015); and T. D. Nguyen et al., *ACS Nano* 4, 2263 (2010).

Figure 3:
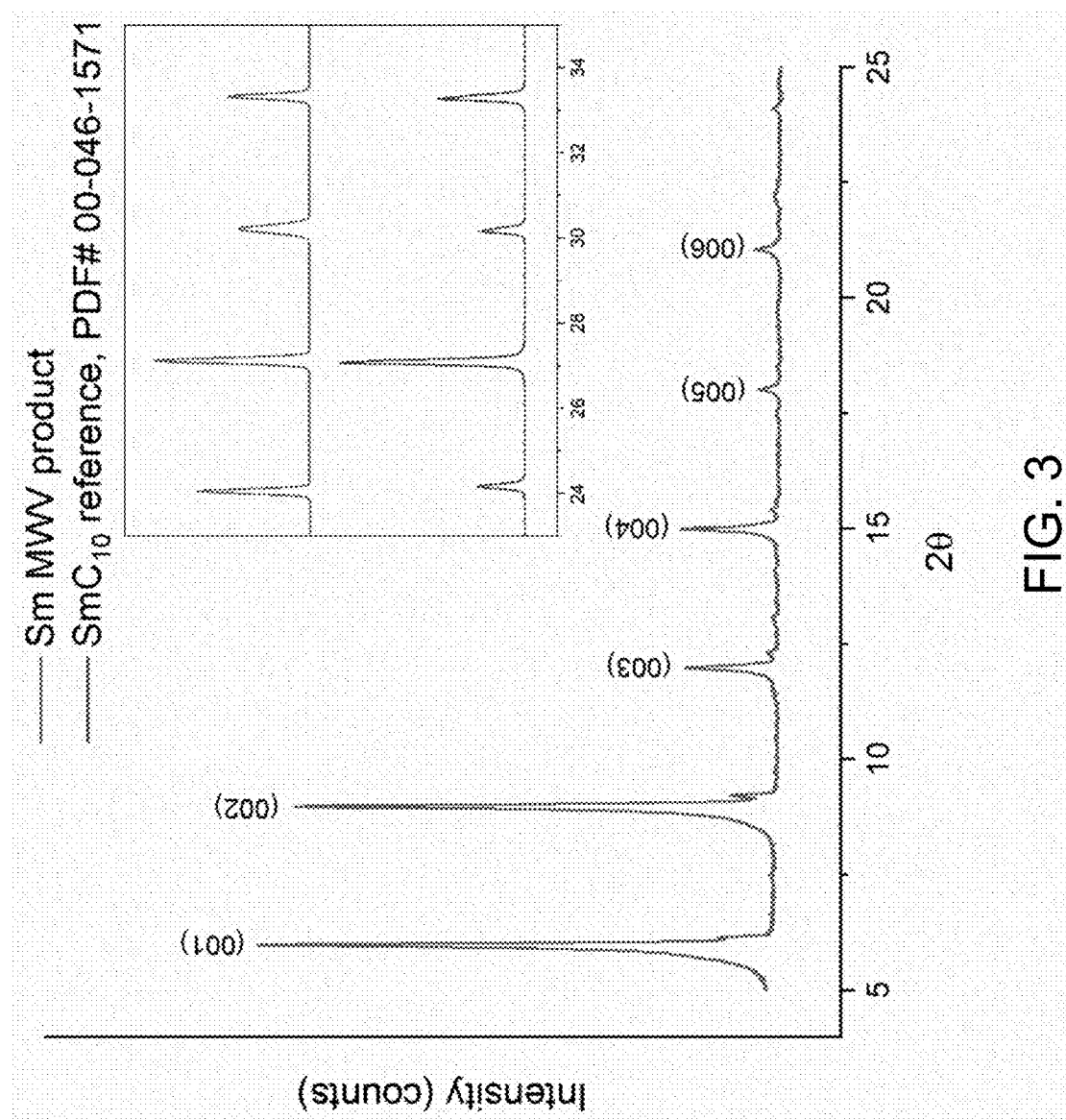
FIG. 3 is a room temperature diffraction pattern of Sm MWV product, which was identified as samarium decanoate ($SmC_{10}$) NPs. Low angle peaks (5-25°) were indexed to successive (00/) Bragg reflections from the lanthanide alkanoate lamellar structure. The inset shows good agreement between the $SmC_{10}$ NPs powder pattern and the $SmC_{10}$ reference pattern, which was only collected in the high angle region (20-50°).

Based on this analysis, the MWV-synthesized nanoparticles were assigned to the lanthanide decanoate ($LnC_{10}$) phase and are referred to hereafter as $LnC_{10}$ NPs. The $SmC_{10}$ NPs powder diffraction data shown in FIG. 3 was indexed to the samarium decanoate reference pattern (PDF #00-046-1571) that was only collected from 20-50°. See K. N. Mehrotra et al., *Monatsh. Chem.* 120, 1063 (1989). The lower angle peaks (5-25°) were indexed as successive (00*l*) Bragg reflections from the lamellar structure. See T. D. Nguyen et al., *ACS Nano* 4, 2263 (2010).

Figure 4B:
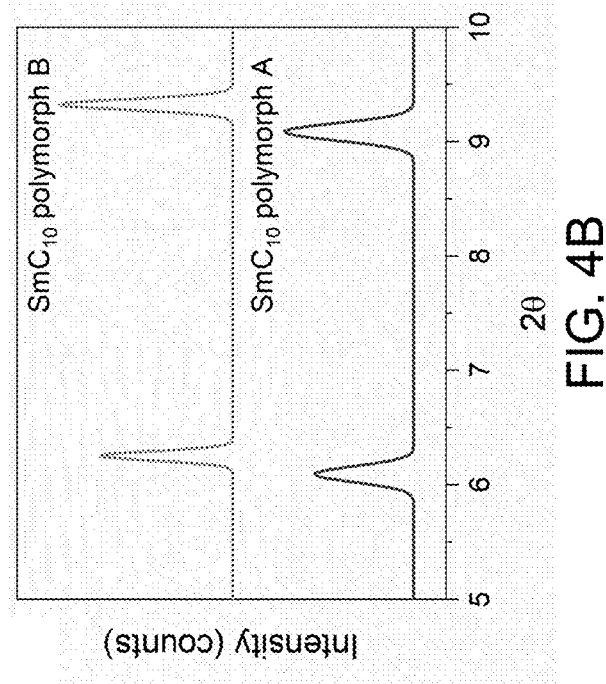
FIG. 4B is a deconvolution of shouldered peaks to show two distinct $SmC_{10}$ polymorphs.
Figure 4A:
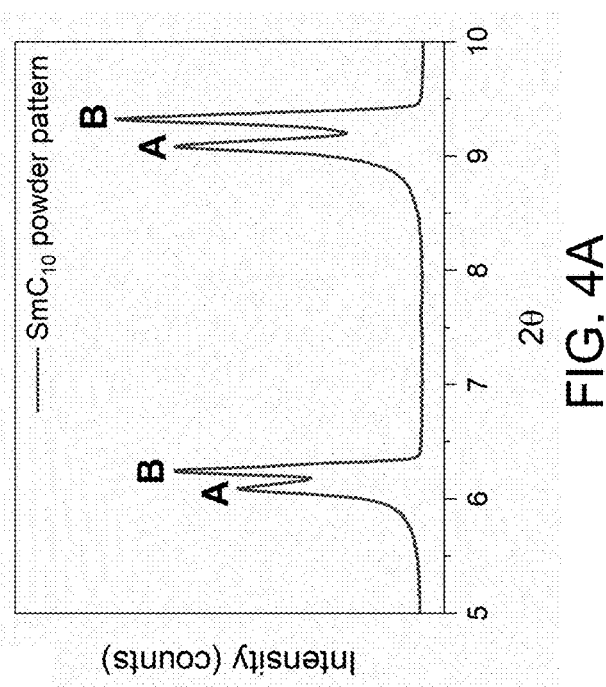
FIG. 4A is a PXRD pattern of $SmC_{10}$ NPs with shouldered low-angle peaks indicating the presence of multiple stable polymorphs.
Figure 4C:
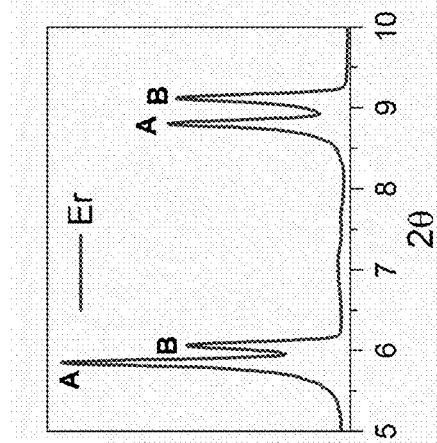
FIGS. 4C, 4D, and 4E show PXRD patterns for Eu, Gd, and $ErC_{10}$ NPs, which also show shouldering. The occurrence of polymorphism only in the smaller lanthanides (Ln=Sm, Eu, Gd, Er) may result from a decrease in thermal stability caused by lanthanide contraction.
Figure 4D:
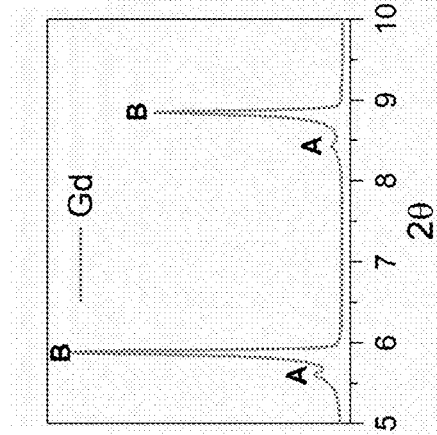
Figure 4E:
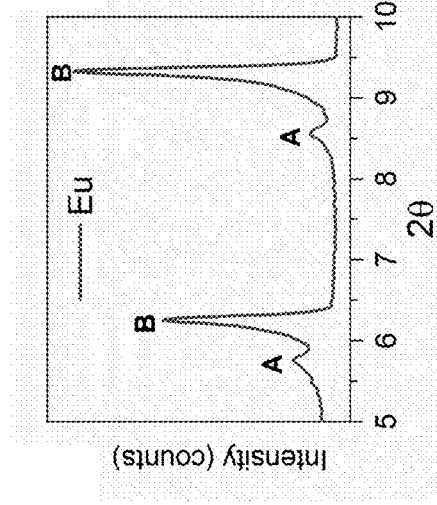

Inspection of low angle regions (5-10°) in the diffraction patterns of certain $LnC_{10}$ NPs reveals shouldered or split peaks. In the magnified spectrum of $SmC_{10}$ NPs shown in FIG. 4A, shoulders on the high intensity peaks are clearly visible. These features most likely indicate the presence of multiple stable polymorphs, which are observed in lanthanide decanoates when variations in the lanthanide-oxygen coordination result in the adoption of a different lattice structure. See F. J. Martinez-Casado et al., *Phys. Chem. Chem. Phys.* 19, 17009 (2017); and S. Carlino and M. J. Hudson, *J. Mater. Chem.* 5, 1433 (1995). The split peaks in the $SmC_{10}$ NPs diffraction pattern can thus be interpreted as the presence of a second crystalline phase and can be deconvoluted into separate diffraction spectra for each polymorph, as shown in FIG. 4B. This phenomenon was also observed in the PXRD patterns of other $LnC_{10}$ NPs (Ln=Eu, Gd, Er), as shown in FIGS. 4C-4E. The occurrence of polymorphism only in the smaller lanthanides may relate to a decrease in thermal stability caused by lanthanide contraction.

Figure 5:
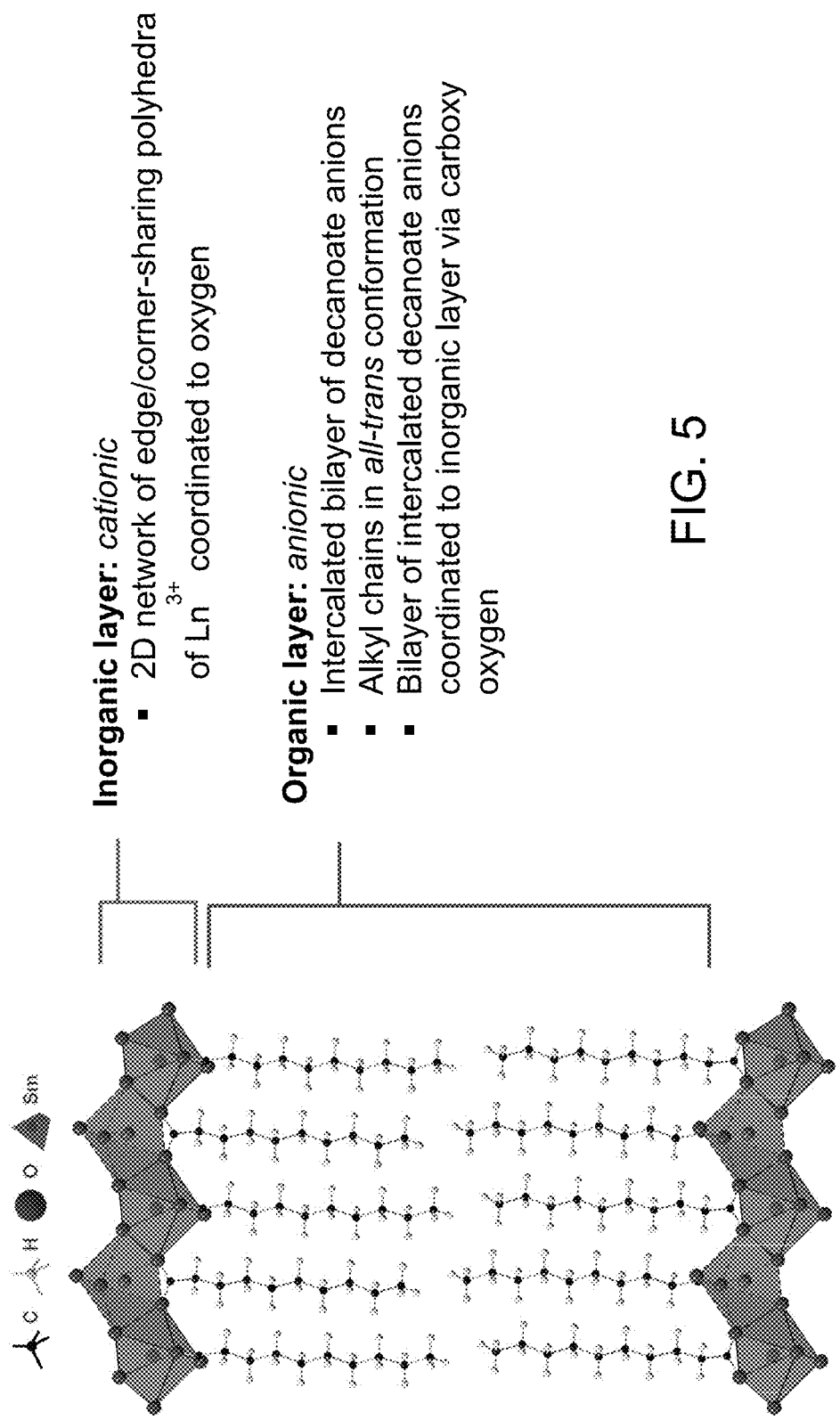
FIG. 5 is an illustration of the lamellar structure of a lanthanide decanoate.

The hybrid nature of alkanoate materials is represented in the diffractions observed in the low- and high-angle regions of the PXRD spectra, which are most significantly influenced by the organic and inorganic components (respectively). Lanthanide decanoates adopt a lamellar structure of distinct organic and inorganic layers, with each $Ln^{3+}$ cation's charge balanced by three $C_9H_{19}COO^-$ anions, as shown in FIG. 5. See H. Li et al., *J. Phys. Chem. B* 109, 21669 (2005). The cationic inorganic layer is a 2D network of edge- and corner-sharing polyhedra that consist of oxygen atoms coordinated to the $Ln^{3+}$ cation. The anionic organic layer is formed by an intercalated bilayer of decanoate anions with alkyl chains in an all-trans conformation. See F. J. Martinez-Casado et al., *J. Therm. Anal. Calorim.* 108, 399 (2012). The decanoate anions coordinate to the $Ln^{3+}$ cation in the inorganic layer via the carboxy oxygen, providing structural stability by sufficiently separating the cationic inorganic layers.

Intercalated decanoate anions can vary their conformation and loading within the lamellar structure. To investigate the configuration of the anions in the $LnC_{10}$ NPs, the observed d-spacing of the (001) PXRD peak was compared to the calculated $d_{max}$ value for a structure with a bilayer of decanoate anions normal to the inorganic layer. The calculated value of $d_{max}$ for the $LnC_{10}$ NPs was found using Equation 2:

$$d_{max}=2d_{C-H}+2(n-1)d_{C-C}(\sin 55°)+2d_{C-O}+2r_{Ln^{3+}} \quad (2)$$

where $d_{C-H}=1.09$ Å, $d_{C-C}=1.54$ Å, $d_{C-O}=1.36$ Å, n=10 (number of carbons in the decanoate alkyl chain), and $r_{Ln}^{3+}$ equals the ionic radii of 9-coordinated trivalent lanthanide cations. See K. Binnemans, *Chem. Rev.* 109, 4283 (2009); and F. J. Martinez-Casado et al., *J. Therm. Anal. calorim.* 108, 399 (2012). The calculated $d_{max}$ value of 29.871 Å for the (001) reflection of the $SmC_{10}$ NPs was in good agreement with the observed value of 29.793 Å, confirming the formation of an intercalated decanoate bilayer with alkyl chains in an all-trans conformation. See E. F. Marques et al., *J. Chem. Soc., Faraday Trans.* 94, 1729 (1998). Close agreement between calculated and observed $d_{max}$ values was also seen for the other $LnC_{10}$ NPs, as shown in Table 1. These values demonstrate a trend of decreasing interlayer spacing as atomic number increases, which is attributed to the contraction of $Ln^{3+}$ ionic radii across the lanthanide series.

TABLE 1

Calculated vs. observed values for interlayer d-spacing ($d_{max}$) of $LnC_{10}$ NPs.
Maximum interlayer spacing values for $LnC_{10}$ NPs

| $Ln^{3+}$ | Ionic radius (Å) | $d_{calc}$ (Å) | $d_{obs}$ (Å) |
|---|---|---|---|
| Pr | 1.179 | 29.965 | 29.875 |
| Nd | 1.163 | 29.933 | 29.813 |
| Sm | 1.132 | 29.871 | 29.793 |
| Eu | 1.120 | 29.847 | 29.870 |
| Gd | 1.107 | 29.821 | 30.221 |
| Er | 1.062 | 29.731 | 29.615 |

Calculated values were computed via Equation 2.
Observed values were taken from the (001) Bragg reflection (~3° 2θ) of the room temperature PXRD pattern for each of the $LnC_{10}$ NPs.
Values for ionic radii were taken from D'Angelo et al. See P. D'Angelo et al., *Inorg. Chem.* 50, 4572 (2011).

Figure 6:
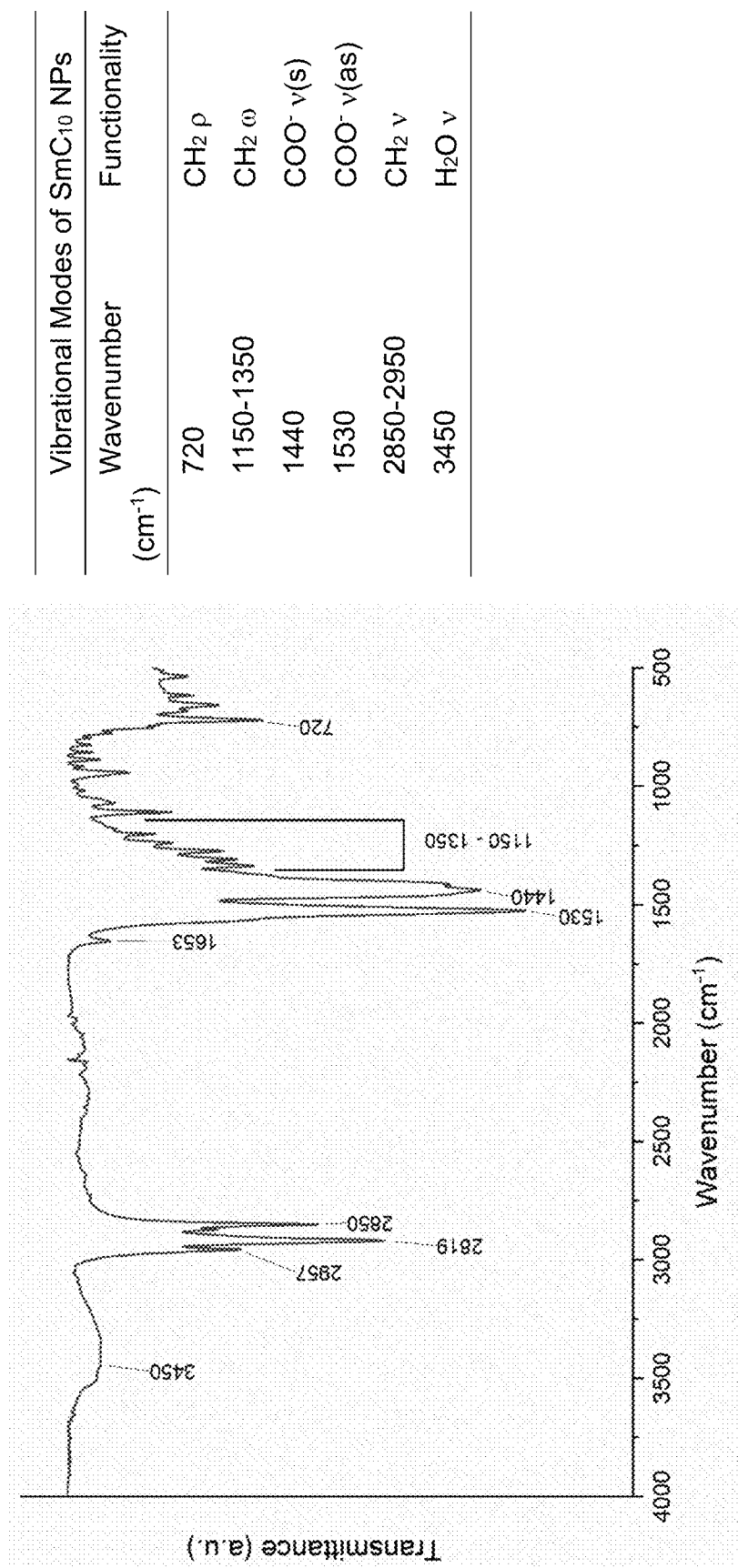
FIG. 6 is an FTIR spectrum of $SmC_{10}$ NPs, with a listing of vibrational modes associated with various functional groups.

In order to further understand the interactions between the decanoic acid and the lanthanide metal, FTIR spectra were collected for all $LnC_{10}$ NPs. A representative FTIR spectrum for $SmC_{10}$ is shown in FIG. 6. The absence of a strong C=O stretching band near 1700 cm$^{-1}$ confirms the lack of free acid within the $SmC_{10}$ NPs. See E. F. Marques et al., *J. Chem. Soc., Faraday Trans.* 94, 1729 (1998). In contrast, the presence of strong bands at 1530 and 1440 cm$^{-1}$ representing the asymmetric and symmetric stretches of COO$^-$ ($v_{as}$ and $v_s$, respectively) indicate bond formation between the oxygen of the decanoate carboxy group and the metal cation. See K. N. Mehrotra et al., *Monatsh. Chem.* 120, 1063 (1989). These bonds can adopt different coordination modes including monodentate, chelating bidentate, or bridging bidentate, which affect their ionic character. See H. A. Ellis et al., *J. Mol. Struct.* 642, 71 (2002). The splitting distance ($\Delta v$) between the two COO$^-$ stretches can be calculated via Equation 3 to determine the coordination mode:

$$\Delta v(cm^{-1}) = v_{as} - v_s \quad (3)$$

For the $SmC_{10}$ NPs, $\Delta v$ was found to be 120 cm$^{-1}$. This indicates a chelating bidentate COO$^-$/Ln$^{3+}$ coordination, which is known to have a largely ionic character. See L. Jongen et al., *Liq. Cryst.* 28, 1727 (2001).

The CH$_2$ and CH$_3$ vibrational modes yield information on the composition and conformation of the decanoate alkyl chains. The presence of long alkyl chains in the $SmC_{10}$ NPs is supported by the strong bands in the 1600-3000 cm$^{-1}$ range, which represent the symmetric and asymmetric stretching modes for the methyl and methylene groups. The progression of regularly spaced bands between 1150-1350 cm$^{-1}$ correspond to the wagging modes of CH$_2$ groups and are often seen in compounds with long aliphatic chains. The shape of the in-phase CH$_2$ rocking mode that appears near 720 cm$^{-1}$ is highly dependent on the lattice structure of the material, with the appearance of a single band typically associated with a monoclinic lattice. See E. F. Marques et al., *J. Chem. Soc., Faraday Trans.* 94, 1729 (1998). The presence of water in the structure was indicated by a broad, low-intensity band centered near 3450 cm$^{-1}$ and a very small band at 1653 cm$^{-1}$. Due to the hydrophobic nature of the long decanoate alkyl chains, this water is most likely adsorbed rather than intercalated into the inorganic layer. The low intensity of the two peaks confirms that the amount of adsorbed water was very small.

Thermogravimetric Analysis

Figure 7B:
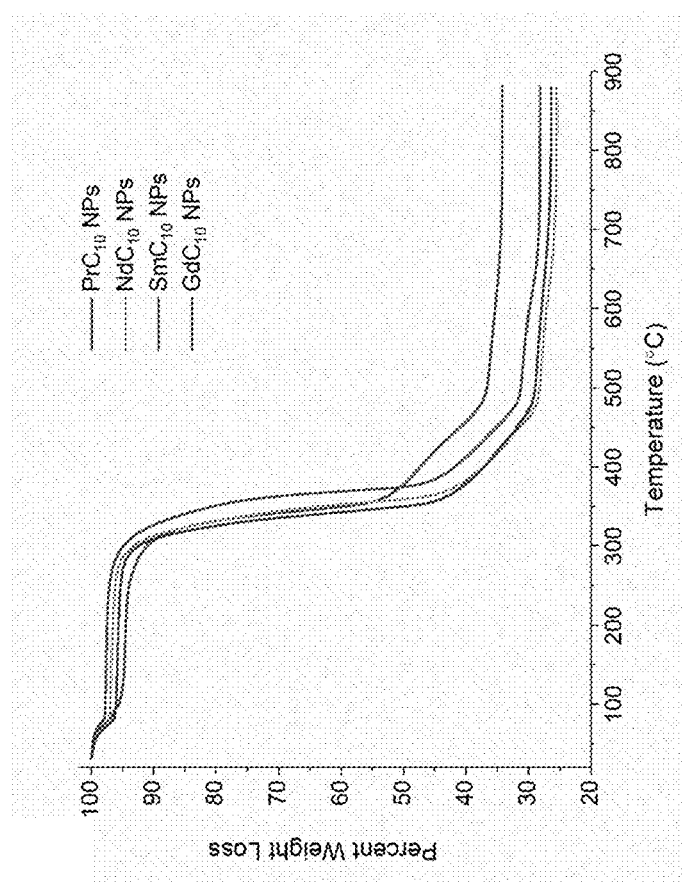
FIG. 7B shows a comparison of TGA weight loss curves for the other $LnC_{10}$ NPs.
Figure 7A:
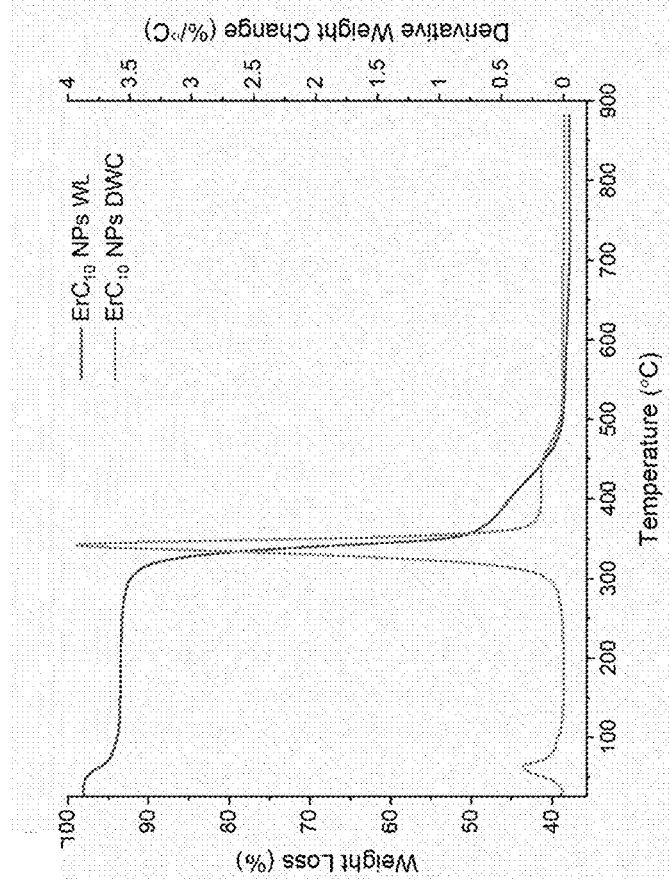
FIG. 7A is a plot of TGA curves of $ErC_{10}$ NPs showing percent weight loss (WL) and derivative weight change (DWC).

TGA was conducted to investigate the thermal behavior of the $LnC_{10}$ NPs. The weight loss and derivative weight change spectra are represented by the $ErC_{10}$ NPs in FIG. 7A, while percent weight loss over the full temperature range of 25-900° C. for the other $LnC_{10}$ NPs is shown in FIG. 7B. According to this data (summarized in Table 2), all samples experienced three main regions of weight loss. The 2-5% weight reduction observed in the 0-100° C. region most likely corresponds to the loss of water of hydration, which is supported by the FTIR data and previously reported lanthanide alkanoates literature. See M. Karmaoui et al., *Chem. Mater.* 18, 4493 (2006).

The most significant weight loss, ranging from 47-60%, occurs between 100-400° C. Weight loss in this range is attributed to the combustion of the intercalated alkanoate anions in the organic layer to form an intermediate phase, the symmetric ketone caprinone ($C_9H_{19}COC_9H_{19}$). See S. Gai et al. *Chem. Rev.* 114, 2343 (2014). Full decomposition of the layered structure occurs above 400° C., producing CO$_2$ gas and the terminal lanthanide oxide phase. A proposed mechanism for the overall thermal decomposition of $LnC_{10}$ NPs based on these results is given in Equation 4, and is in good agreement published mechanisms for bulk lanthanide alkanoates:

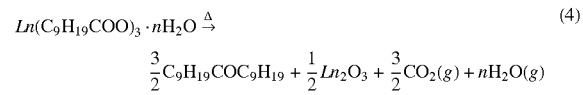

$$Ln(C_9H_{19}COO)_3 \cdot nH_2O \xrightarrow{\Delta}$$
$$\frac{3}{2}C_9H_{19}COC_9H_{19} + \frac{1}{2}Ln_2O_3 + \frac{3}{2}CO_2(g) + nH_2O(g) \quad (4)$$

See S. N. Misra et al., *J. Inorg. Nucl. Chem.* 25, 311 (1963); K. N. Mehrotra et al., *Monatsh. Chem.* 120, 1063 (1989); and M. Karmaoui et al., *Chem. Mater.* 18, 4493 (2006).

The TGA behavior of the $LnC_{10}$ NPs also demonstrates a trend of decreasing thermal stability as Ln$^{3+}$ ionic radius contracts. This is most clearly demonstrated by the significant increase in weight loss by the smaller Ln$^{3+}$ (Sm, Gd, Er) at low temperatures, with $ErC_{10}$ losing more than double the mass of $PrC_{10}$ in the 0-100° C. range (Table 2). In the 400-900° C. range, the noticeable decrease in the weight loss for Sm, Gd, and $ErC_{10}$ NPs can be attributed to greater decomposition activity at lower temperatures. In all samples, negligible weight loss occurred beyond 500° C., which indicates formation of the terminal oxide phase near that temperature. The thermal decomposition behavior and mechanism for the $LnC_{10}$ NPs are both in agreement with literature for bulk lanthanide decanoates. See K. N. Mehrotra et al., *Monatsh. Chem.* 120, 1063 (1989).

TABLE 2

Summary TGA weight loss results for $LnC_{10}$ NPs.
Thermal decomposition: percent weight loss and products for $LnC_{10}$ NPs

| Products $Ln^{3+}$ | Hydrated water 0-100° C. | $C_9H_{19}COC_9H_{19}$ (ketone) 100-400° C. | $CO_2$ 400-500° C. |
|---|---|---|---|
| Pr | 2.2 | 59.7 | 10.5 |
| Nd | 3.0 | 57.0 | 8.8 |
| Sm | 3.9 | 52.3 | 8.2 |
| Gd | 4.4 | 48.3 | 10.6 |
| Er | 5.1 | 47.0 | 10.1 |

Weight loss occurred in three main regions due to the loss of water of hydration (0-100° C.), followed combustion of the intercalated decanoate anions to form the intermediate ketone caprinone (100-400° C.), and finally full decomposition of the layered structure to produce $CO_2$ gas and the terminal oxide $Ln_2O_3$ (400-500° C.).
Decomposition of the lanthanide alkanoate phase into the lanthanide oxide was complete by 500° C., and no significant weight loss was observed above that temperature.

In order to validate the proposed mechanism of Equation 4, dried samples of $LnC_{10}$ NPs were calcined in air at 500°

Figures 8A, 8B, 8C, 8D, 8E:
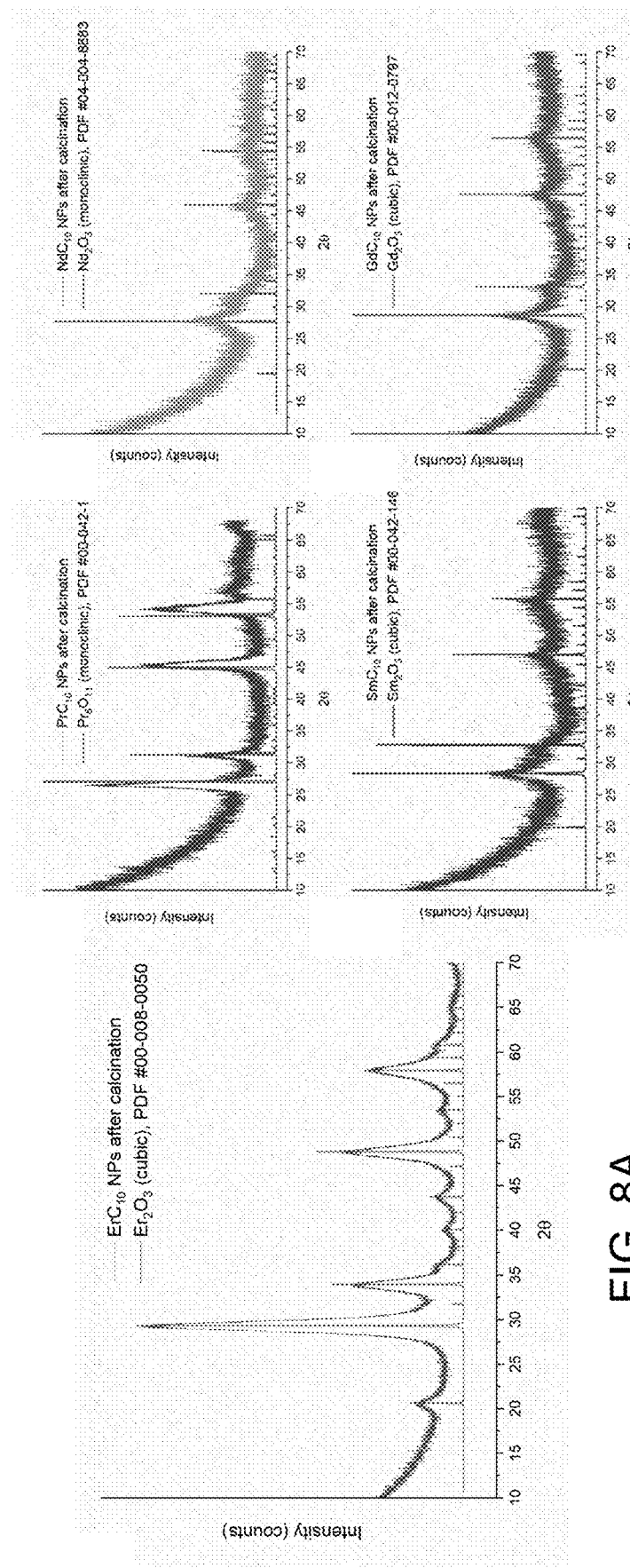
FIG. 8A is a powder X-ray diffraction pattern of calcined $ErC_{10}$ NPs vs. $Er_2O_3$ reference pattern, verifying decomposition of the lanthanide alkanoate to the cubic oxide phase after calcination in air at 500° C. for 1 h. Calcination of other $LnC_{10}$ NPs also produced lanthanide oxides, with calcined Pr, Nd, Sm, and $GdC_{10}$ NPs forming.
FIG. 8B, monoclinic $Pr_6O_{11}$.
FIG. 8C, monoclinic $Nd_2O_3$.
FIG. 8D, cubic $Sm_2O_3$.
FIG. 8E, cubic $Gd_2O_3$ phases.
Figure 9:
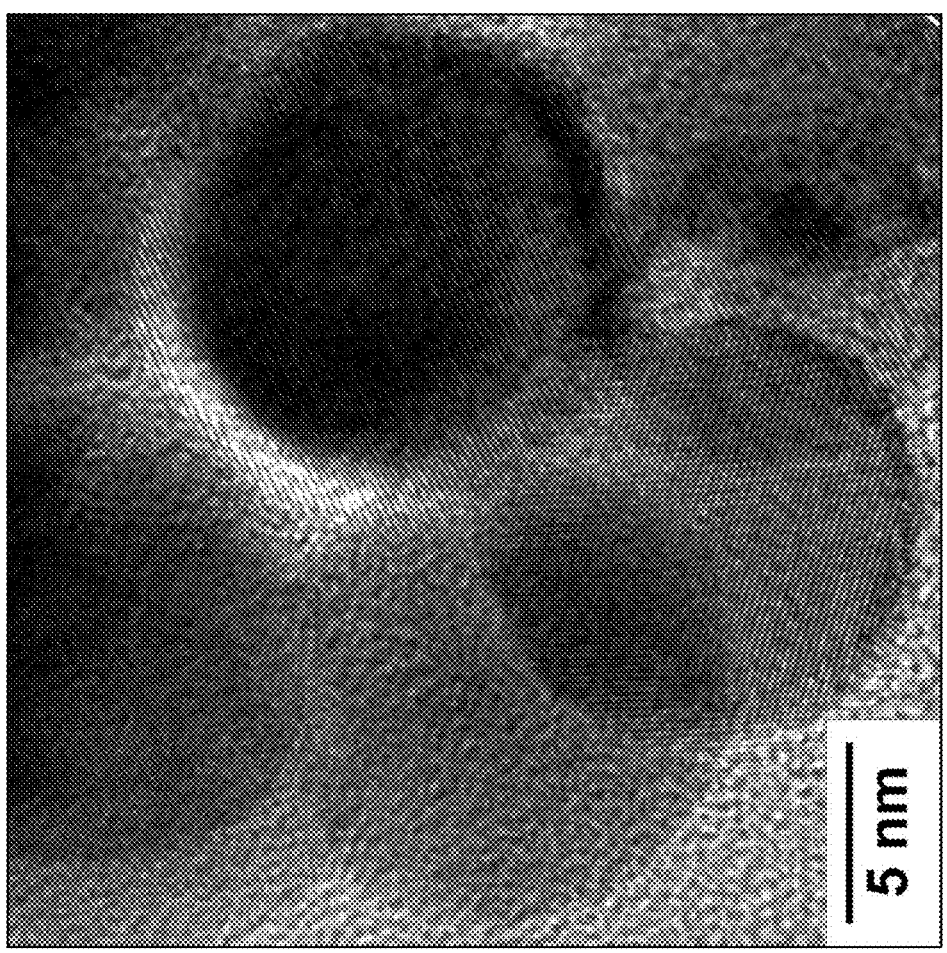
FIG. 9 is a transmission electron micrograph of $Sm_2O_3$ NPs produced by calcination of $SmC_{10}$ NPs at 500° C. for 1 h. The spherical morphology was not affected by calcination, but a significant reduction in particle diameter was observed.

C. for 1 h. TGA data suggested that calcination at this temperature should result in the complete decomposition of $LnC_{10}$ NPs into the oxide phase. As represented by the diffraction patterns of $ErC_{10}$ NPs before and after calcination, shown in FIG. 8A, PXRD analysis confirmed the conversion of the alkanoate to the cubic $Er_2O_3$ phase. The diffraction patterns of the other $LnC_{10}$ NPs also showed successful conversation to the oxide phase after calcination, shown in FIGS. 8B to 8E. Comparison with reference patterns indicated that the monoclinic oxide phase was formed by $Pr_6O_{11}$ and $Nd_2O_3$, while $Sm_2O_3$ and $Gd_2O_3$ adopted the cubic oxide phase. See W. E. Swanson, *Standard X-ray Diffraction Powder Patterns*, National Bureau of Standards, Washington, D.C., (1974); J. Zhang et al., *J. Solid State Chem.* 122, 53 (1996); M. Langlet and R. D. Shannon, *Thin Solid Films* 186, L1 (1990); and K. Martin and G. McCarthy, *ICDD Grant-in-Aid*, North Dakota State University, Fargo, North Dakota, USA (1991).

As represented by the electron micrograph of $Sm_2O_3$ NPs, shown in FIG. 8, TEM analysis of the oxide products showed that nanoparticle morphology was not affected by calcination. All calcined $Ln_xO_y$ NPs displayed the same monodispersed spherical morphology that was observed for the decanoate phases. In contrast to the lack of morphological impact, calcination caused a significant reduction in particle diameter of the $Ln_xO_y$ NPs in comparison to the $LnC_{10}$ NPs. Measurements of $Ln_xO_y$ NPs size, collected via TEM image analysis, ranged from 13.4 nm ($Pr_6O_{11}$) to 3.1 nm ($Er_2O_3$), with an overall average diameter of 6.8 nm. This value represents a tenfold reduction from the decanoate phase, which supports the conversion of $LnC_{10}$ to $Ln_xO_y$ via combustion of intercalated decanoate ligands. This is also in agreement with the proposed thermal decomposition mechanism described by Equation 4. The large loss in particle diameter suggests that the $LnC_{10}$ NPs may have porous surfaces and/or interiors, which could facilitate the removal of internal layers and result in the contraction observed after calcination.

Photoluminescence of Lanthanide Decanoate Nanoparticles

The optical properties of the $LnC_{10}$ NPs were characterized via UV-Vis and photoluminescence (PL) spectroscopy. UV-Vis absorbance spectra for all $LnC_{10}$ NPs had maxima at ~215 nm, with Er and $EuC_{10}$ NPs showing a second, less intense absorbance around 570 nm. These absorbances represent transitions of photoexcited electrons from the ground state to higher-energy excited states in the $Ln^{3+}$ ions. See F. Chen et al., *J. Alloys Compd.* 664, 311 (2016). In comparison, peaks in the PL emission spectrum are generated by the radiative relaxation of electrons from various excited states within the lanthanide 4f shell. See F. Chen et al., *J. Alloys Compd.* 664, 311 (2016); and Y. Hasegawa et al., *NPG Asia Mater.* 10, 52 (2018). As represented by the PL emission spectra for the Er, Sm, and $EuC_{10}$ NPs, shown in FIGS. 10A-D, each $Ln^{3+}$ cation possesses a different configuration of 4f energy levels that generates a unique narrow line emission spectrum (spectra for Pr, Nd, and $GdC_{10}$ NPs are presented in FIGS. 11A-D). The electronic transitions are highly sensitive to the environment of the $Ln^{3+}$ cation, which can be observed as variations in the wavelength, shape, and intensity of PL emission bands from the expected emission spectra. See S. V. Mahajan and J. H. Dickerson, *Nanotechnology* 18 (2007); and F. Geng et al., *Inorg. Chem.* 48, 6724 (2009); and R. Si et al., *Chem. Int. Ed.* 44, 3256 (2005).

Figure 10A:
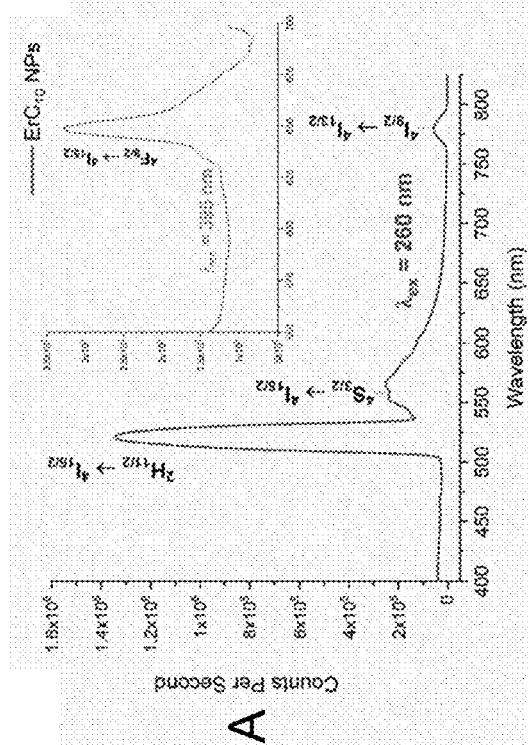

For example, the typical $Er^{3+}$ emission spectrum exhibits intense green and red peaks in the 500-550 and 640-670 nm ranges, respectively. See S. Gai et al., *CrystEngComm* 13, 5480 (2011). Transitions to the $^4I_{15/2}$ $Er^{3+}$ ground state from the $^2H_{11/2}$ and $^4S_{3/2}$ excited states produce the green emission, and the $^4F_{9/2} \rightarrow ^4I_{15/2}$ transition generates the red emission. As seen in FIG. 10A, the $^4F_{9/2}$ red line emission is absent from the $ErC_{10}$ NPs PL spectrum collected from $\lambda_{ex}$=260 nm. The emission can be observed by increasing the excitation wavelength ($\lambda_{ex}$=395 nm), but its intensity is more than two orders of magnitude lower than that of the green line emissions (see FIG. 10A, inset). This selective variation in emission intensity may be related to increased surface quenching effects that are known to occur in nanoscale materials. See H. Qiu et al., *J. Mater. Chem.* 21, 17202 (2011). The CIE (Commission Internationale de l'Eclairage 1931) chromaticity diagrams in FIGS. 12A and 12B display the green and orange emission colors calculated from the $ErC_{10}$ NPs PL spectra collected at $\lambda_{ex}$=260 nm and 395 nm, respectively.

Figure 10B:
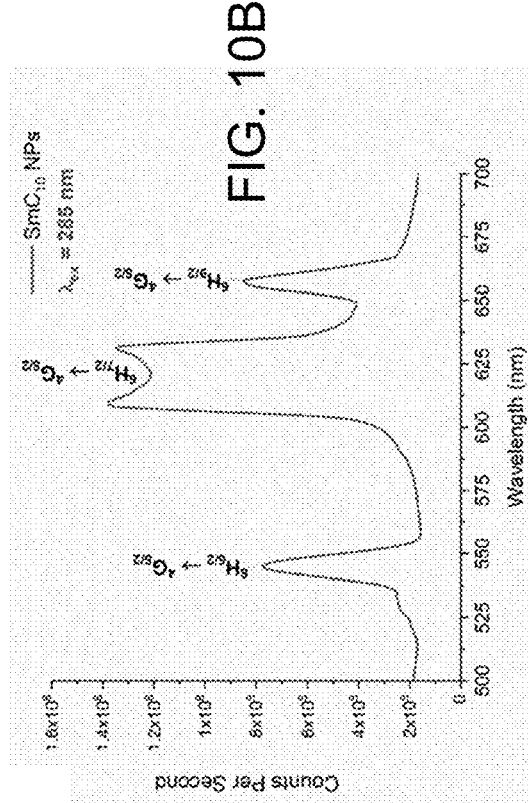

The PL spectrum of the $SmC_{10}$ NPs, shown in FIG. 10B, has no notable absences among the expected emission lines. Upon excitation at 285 nm, the $SmC_{10}$ NPs produced three major emission bands, with the most intense $^6H_{7/2} \rightarrow ^4G_{5/2}$ transition producing split peaks at 609 and 631 nm. This spectrum and its corresponding orange CIE coordinates (FIG. 12A) are in good agreement with reported Sm luminescent materials. See Y. Hasegawa et al. *NPG Asia Mater.* 10, 52 (2018); and H. Qiu et al., *J. Mater. Chem.* 21, 17202 (2011). The peak splitting is consistent with nanoscale effects on lanthanide optical properties. See G. Jia et al., *J. Phys. Chem. C* 113, 153 (2009).

Figure 10C:
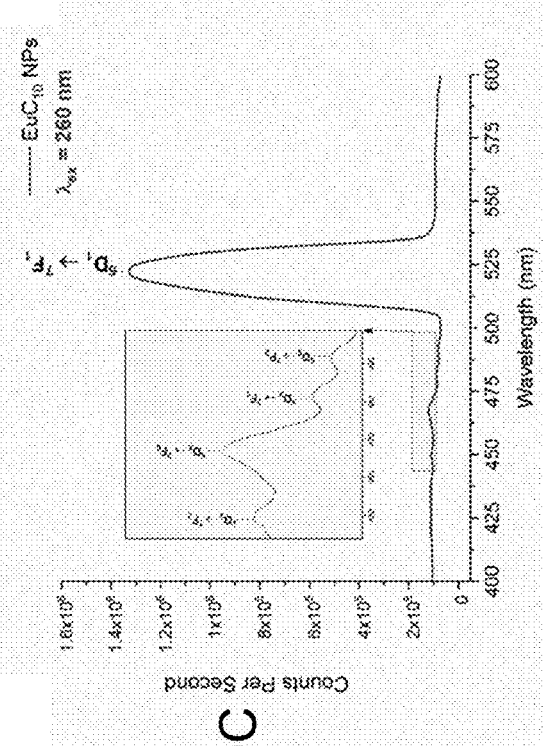
Figure 10D:
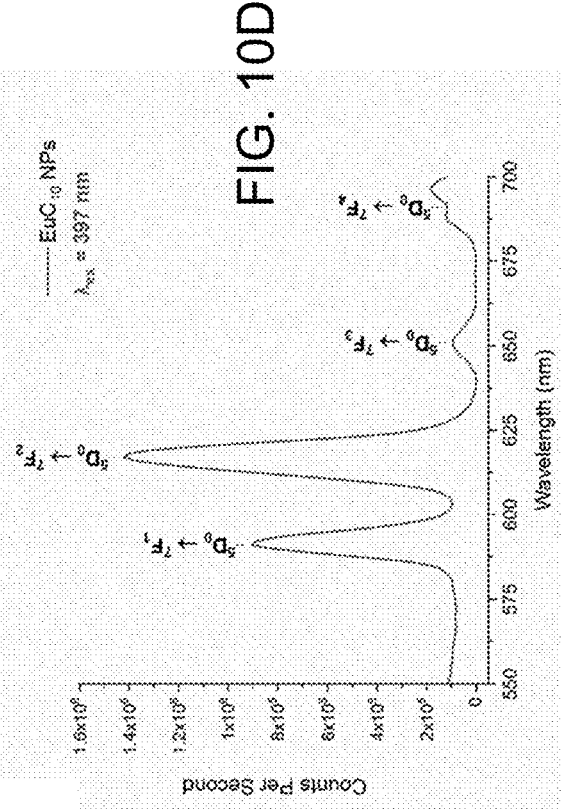
Figure 11A:
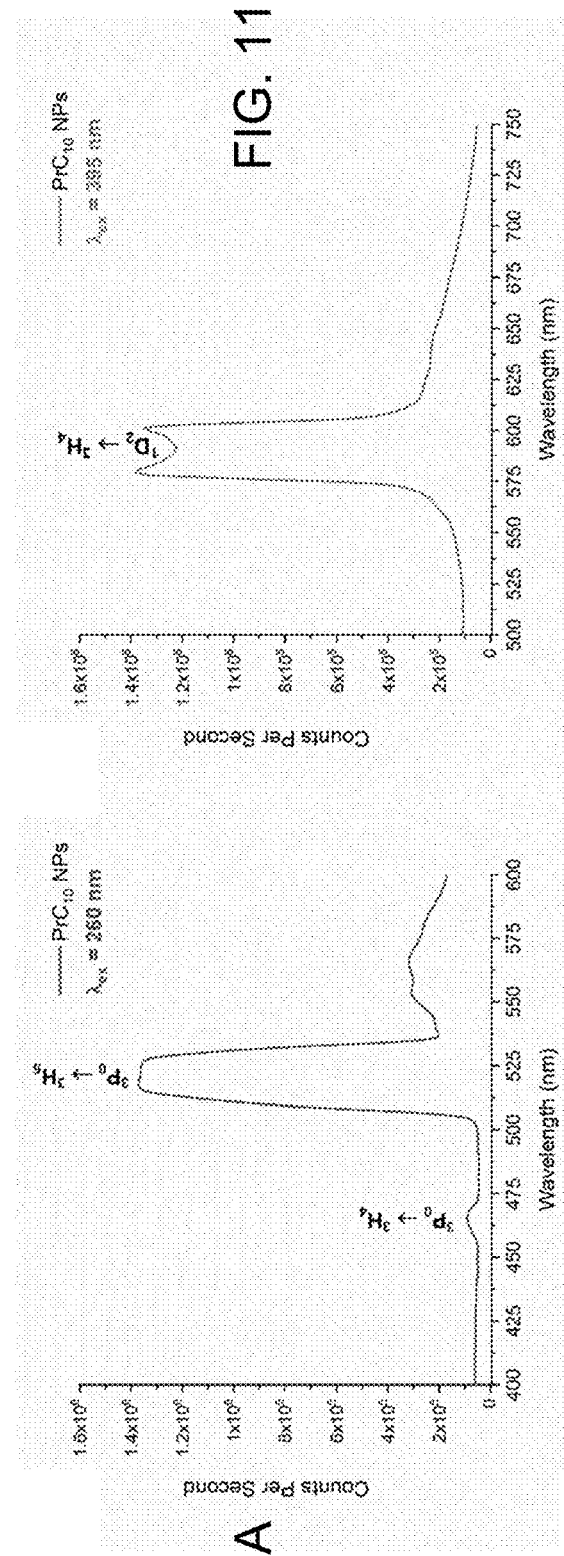
Figure 11B:
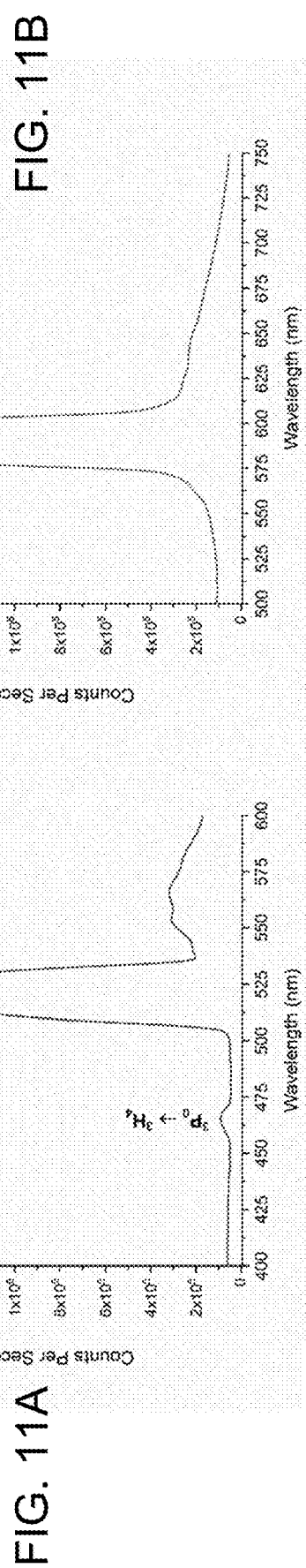
Figure 11C:
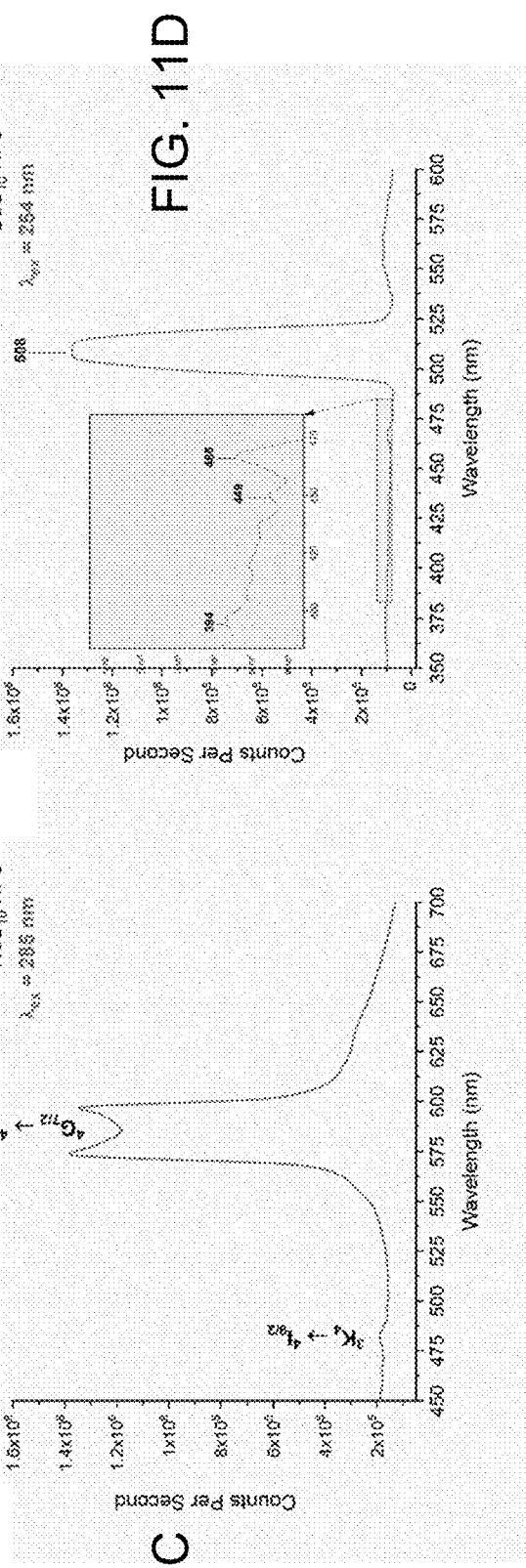
Figure 11D:
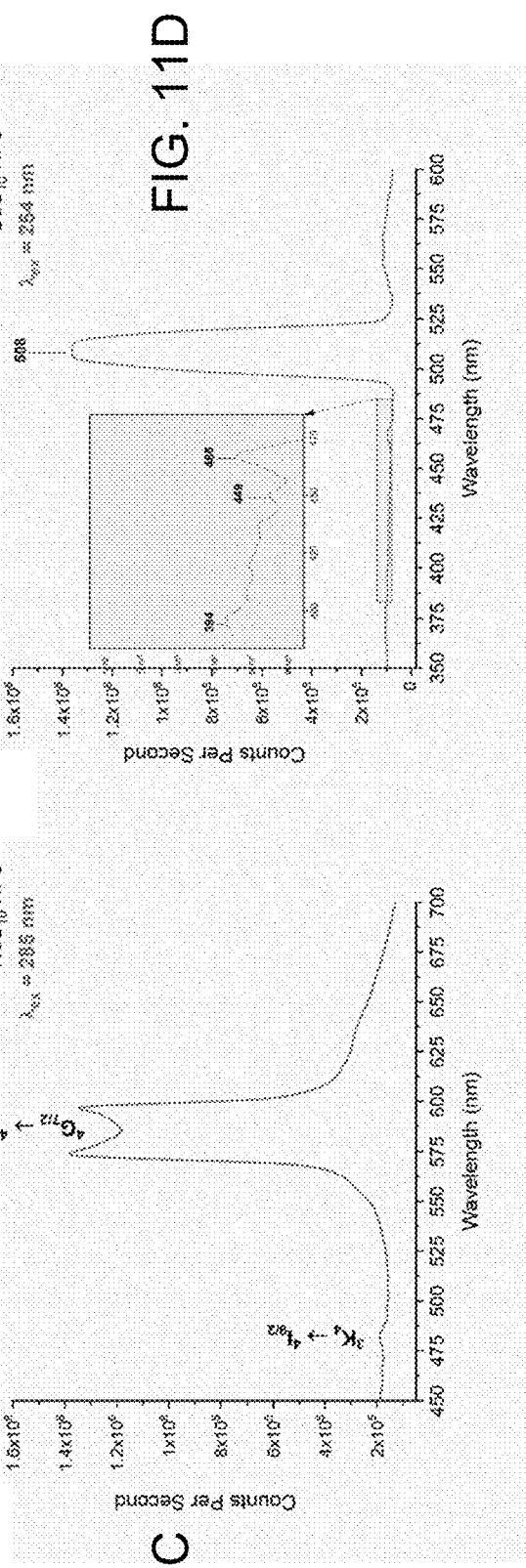

FIG. 10C shows the $EuC_{10}$ NPs PL emission spectrum collected at $\lambda_{ex}$=260 nm, which features transitions from higher-level $^5D_K$ excited states (K=1, 2, 3) to various $^7F_J$ energy levels (J=0, 1, 2, 3). See S. V. Mahajan and J. H. Dickerson, *Nanotechnology* 18 (2007). The highest intensity $^5D_1 \rightarrow ^7F_1$ transition occurs at 525 nm, producing a green emission that corresponds to the CIE coordinates seen in FIG. 12A. Increasing the excitation wavelength to 395 nm populates the $^5D_0$ excited states, generating four main bands from radiative relaxation to $^7F_J$ states (J=1, 2, 3, 4) (FIG. 10B). This emission spectrum is dominated by the hypersensitive $^5D_0 \rightarrow ^7F_2$ transition, which produces a bright red emission at 617 nm. The high intensity of this emission by the $EuC_{10}$ NPs is characteristic of Eu-containing nanomaterials, in which a reduction in $Eu^{3+}$ site symmetry produces an energetically favorable arrangement for radiative transitions. See Y. Hasegawa et al., *NPG Asia Mater.* 10, 52 (2018); and B. V. Rao et al., *Mater. Lett.* 61, 2868 (2007). The increased intensity of the red $^5D_0 \rightarrow ^7F_2$ emission relative to the orange $^5D_1 \rightarrow ^7F_1$ emission by the $EuC_{10}$ NPs results in a higher color chromaticity that is preferred for luminescent $Eu^{3+}$ materials (see FIG. 12B). See G. Gia et al., *J. Phys. Chem. C* 113, 153 (2209). In order to assess the presence of optical activity in the NIR region PL emission spectra were collected from 700-1550 nm for $LnC_{10}$ NPs with known NIR emissions (Ln=Pr, Nd, Sm, Er). NIR emissions at wavelengths corresponding to expected transitions were observed for each sample.

Figure 12B:
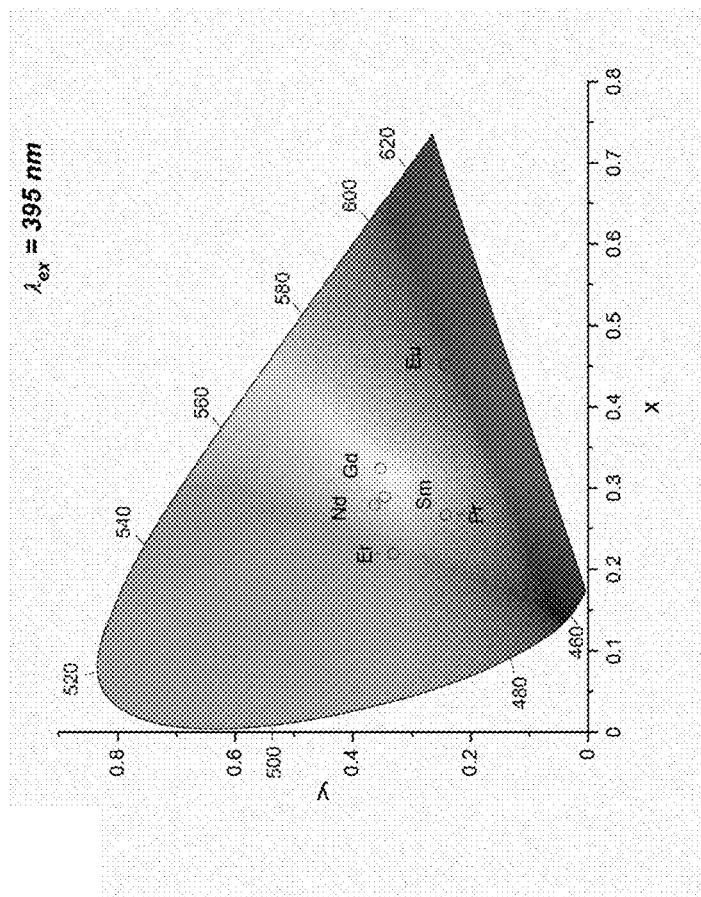
FIGS. 12A and 12B are chromaticity CIE diagrams calculated from photoluminescence emission spectra.
Figure 12A:
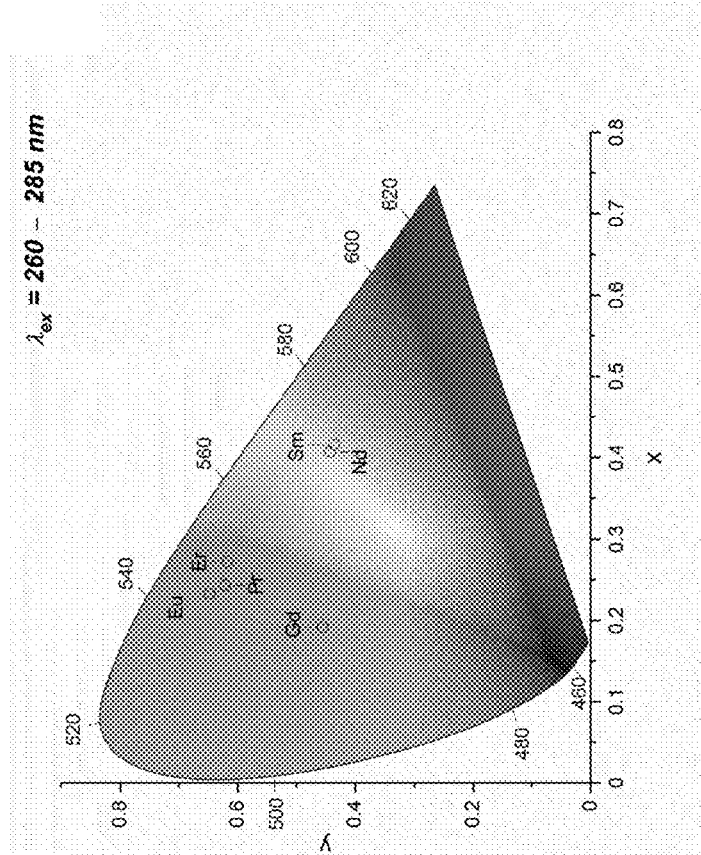
Figure 13:
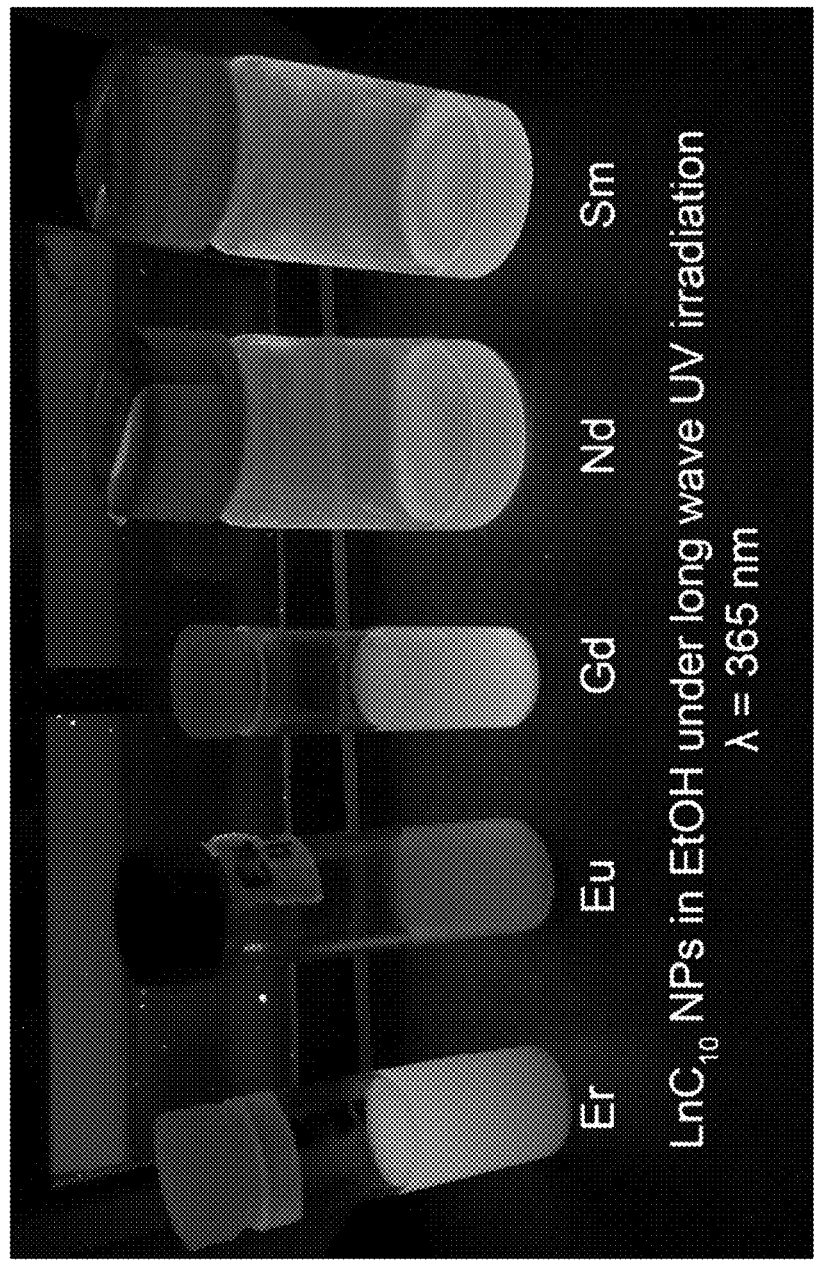
FIG. 13 shows visible photoluminescence under long-wave UV irradiation ($\lambda$=365 nm) for colloidal suspensions of $LnC_{10}$ NPs: Er, Eu, Gd, Nd, and Sm. The observed colors correspond to the CIE x, y coordinates calculated for PL emission spectra excited at 395 nm (FIGS. 10 and 11).
Figure 16A:
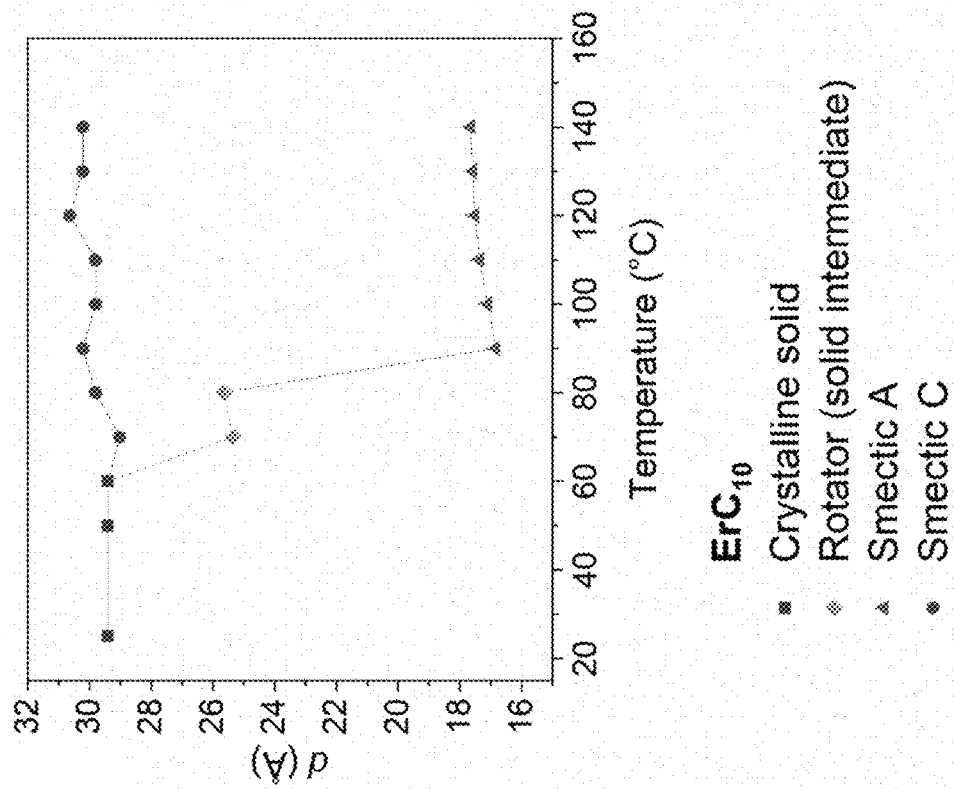
Figure 16B:
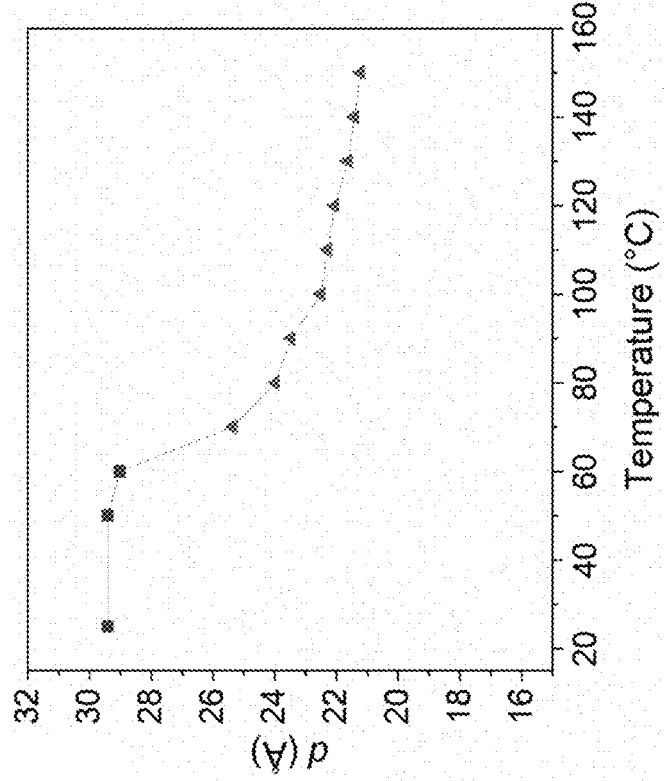

Under long-wave UV irradiation ($\lambda$=365 nm), colloidal dispersions of Er, Eu, Gd, Nd, and $SmC_{10}$ NPs produced bright visible luminescence, as shown in FIG. 13. All the colors of visible luminescence corresponded to the CIE coordinates calculated from PL emission spectra collected at $\lambda_{ex}$=395 nm (FIG. 12B). The high optical activity observed in the $LnC_{10}$ NPs is a significant contrast to the results for bulk lanthanide alkanoates in literature. In their study of bulk europium alkanoates (C=16), Li et al. reported a significant reduction in PL emission intensity by $EuC_{16}$ compared to other Eu-containing materials. They also stated that long-wave UV irradiation did not produce any visible luminescence from $EuC_{16}$, attributing the lack of optical activity to the non-radiative quenching of photoexcited $Eu^{3+}$ electrons by closely lying $\pi^*$ orbitals of the COOH groups. See H. Li et al., *J. Phys. Chem. B* 109, 21669 (2005). Other groups have activated luminescence in liquid crystalline or vitrified glass phases, but there are no previous reports of high optical activity by room temperature, as-synthesized lanthanide alkanoates. See R. W. Corkery and J. P. D. Martin, *J. Lumin.* 82, 1 (1999); and K. Binnemans et al., *Phys. Chem. Chem. Phys.* 3, 10 (2001).

It was hypothesized that the reason bulk alkanoates have little to no photoluminescence activity in comparison to the nanoscale decanoates relates to the differences in $Ln^{3+}$ ion coordination at the distinct size regimes. See Y. Kitagawa et al., *Inorg. Chem.* 59, 5865 (2020). At the bulk scale, dense packing of decanoate bilayers would promote strong internal quenching of photoexcited lanthanide electrons by the nearby ligand carboxylate groups. A different environment is experienced by surface lanthanide atoms, which are far more prevalent in nanoscale materials and have a lower coordination number as a result of reduced site symmetry. See S. V. Mahajan and J. H. Dickerson, *Nanotechnology* 18 (2007). This change in coordination environment at the nanoscale could effectively reduce the number of nearby carboxylate groups able to provide energetically favorable pathways for non-radiative deactivation. As a result, photoexcited $Ln^{3+}$ electrons could more freely undergo emission-generating radiative transitions.

Mesomorphic Behavior of Lanthanide Decanoate Nanoparticles

Thermal analysis via DSC and HT-PXRD was performed in order to detect the formation of liquid crystalline phases by the $LnC_{10}$ NPs. Confirmation and identification of mesomorphic phases in crystalline solids is also typically carried via polarized light microscopy (PLM). However, PLM analysis of lanthanide alkanoates is seldom reported in detail and is not used to independently verify liquid crystalline phase or behavior. This is due to the difficulty in obtaining good defect or optical texture from lanthanide alkanoates, which become highly viscous near the phase transition point and have a strong tendency to align homeotropically that interferes with observation of birefringence. See E. F. Marques et al., *J. Chem. Soc., Faraday Trans.* 94, 1729 (1998).

Differential Scanning Calorimetry

DSC analysis was performed on the $LnC_{10}$ NPs (Ln=Pr, Nd, Sm, Gd, Er) to investigate the presence of thermotropic liquid crystalline (LC) mesophases, which can be identified by key features in the DSC spectra. As shown in FIGS. 14A-E, DSC spectra of all $LnC_{10}$ NPs collected during the first heating cycle (0-200° C.) showed 2-3 strong endothermic events, with the temperature of the first peak displaying a general decrease with increasing atomic number. Comparison against TGA spectra confirm that these heat flux events were not associated with thermal decomposition and can thus be assigned to phase transitions.

The highest-intensity peak on each DSC thermogram was identified as the primary mesophase transition, or liquid crystalline phase formation. For the larger lanthanides (Pr and Nd), the mesophase transition was the first peak, which implies a direct transition to the liquid crystalline phase without pre-melting phenomena (FIGS. 14D-E). See E. F. Marques et al., *J. Chem. Soc., Faraday Trans.* 94, 1729 (1998). In contrast, the smaller lanthanides (Sm, Gd, Er) showed lower-enthalpy peaks before the mesophase transition (FIGS. 14A-C). This is consistent with a stepwise melting process, in which one or more intermediate phases form before the primary phase transition. The DSC thermograms of all $LnC_{10}$ NPs showed an additional phase transition with lower enthalpy after the main peak and displayed a trend of decreasing peak temperature with increasing atomic number. Based on the position and enthalpy of the main endothermic peak as well as the expected phase transition behavior for lanthanide alkanoates, the main transition was identified as the formation of a Smectic A (SmA) liquid crystalline phase during the melting process of the solid crystalline (Cr) phase into an isotropic liquid (IL). See E. F. Marques et al., *J. Chem. Soc., Faraday Trans.* 94, 1729 (1998); and K. Binnemans et al., *Inorg. Chem.* 39, 5938 (2000). The higher-temperature phase transition (occurring after Cr→SmA) was identified as the clearing point, or formation of the fully melted isotropic liquid.

The DSC spectra shown in FIGS. 14A-E illustrate the significant influence of lanthanide identity and ionic radius on the $LnC_{10}$ NPs thermal behavior. As seen in FIGS. 14A-C, the DSC curves of the smaller lanthanides $LnC_{10}$ NPs (Ln=Sm, Gd, Er) show distinct features that were not observed for the larger lanthanides. For example, the $SmC_{10}$ NPs curve pictured in FIG. 14A shows a distinct peak at 78° C., followed by a more intense shouldered peak over the 85-105° C. range, and finally a sharp peak at 134° C. These features represent a multistep melting process caused by the formation of a solid intermediate (SI) phase during the SmA phase transition. This SI phase, which is known as a "rotator phase" due to the type of movement displayed by its partially melted alkyl groups, is characterized by stepwise conformational changes and defect formation in the alkyl chains. See F. J. Martinez-Casado et al., *J. Therm. Anal. Calorim.* 50, 399 (2012). The SI phase and multistep melting can also be observed between ~70-140° C. in DSC curves of the $GdC_{10}$ and $ErC_{10}$ NPs (FIGS. 14B and 14C).

The DSC curves of the $NdC_{10}$ and $PrC_{10}$ NPs (FIGS. 14D and 14E) demonstrate the expected thermal behavior for larger lanthanide alkanoates. Strong endothermic peaks near 90° C. indicate a direct transition between the Cr and SmA phases, without the formation of the SI intermediate. In the next transition (130-140° C.), the SmA phase loses long-range order to become an isotropic liquid (IL) phase. During the first cooling cycle, events corresponding to clearing (IL→SmA) and recrystallization (SmA→Cr) were observed for both $PrC_{10}$ and $NdC_{10}$ NPs. In contrast, the cooling cycle of the $SmC_{10}$ and showed only one event (IL→Cr), which had a significantly lower onset temperature compared to the $PrC_{10}$ and $NdC_{10}$ NPs. This may be related to a more complete melting of the $SmC_{10}$ NPs alkyl chains due to its lower thermal stability, hindering the restoration of long-range order needed for complete recrystallization. This phenomenon is known to occur for lanthanide alkanoates with smaller $Ln^{3+}$ ionic radii. See H. Li et al., *J. Phys. Chem. B* 109, 21669 (2005). The $GdC_{10}$ and $ErC_{10}$ NPs did not show any activity during the cooling cycle.

The enthalpy changes (ΔH) for each endothermic transition were calculated and can be seen in Table 3. For all $LnC_{10}$ NPs, ΔH values for the solid to LC transition were much larger than those for the transition from LC to ionic liquid phases. For the larger lanthanide LnC$_{10}$ NPs (Ln=Pr and Nd), the enthalpy of the Cr→SmA transition was greater than the SmA→IL transition by a factor of 10. Smaller lanthanide SmC$_{10}$ and GdC$_{10}$ NPs underwent multiple intermediate transitions, with the initial Cr→SI (rotator) transition appearing in conjunction with the SI→SmA transition as a split or shoulder on before the main peak. Interestingly, the peaks representing SmA formation by the ErC$_{10}$ NPs were distinct and isolated (FIG. 14C). As seen in Table 3, the enthalpy of the LC-forming SI→SmA transition was triple that of the preceding Cr→SI enthalpy for the ErC$_{10}$ NPs.

In summary, thermal analysis of the LnC$_{10}$ NPs via DSC indicated the formation of liquid crystal phases for all nanoscale lanthanide samples (Ln=Pr, Nd, Sm, Gd, Er). See K. Binnemans and C. Gorller-Walrand, *Chem. Rev.* 102, 2303 (2002). The DSC results also demonstrate that at the nanoscale, LC phases are present even for very small Ln$^{3+}$ such as Er. Table 3 displays the temperature and enthalpy values for each transition, as calculated from the DSC data.

alkyl conformation. See K. Binnemans et al., *Inorg. Chem.* 39, 5938 (2000). The first solid to mesophase transition is identified as the melting of the alkyl chains and can be observed via HT-PXRD as a distinct decrease in the d-spacing values of the low angle peaks. This can be seen in the comparison between room temperature and 90° C. diffraction patterns of the Pr and NdC$_{10}$ NPs (FIGS. 15A and 15B). The shift of the first reflection to higher angles as well as the loss of the third-order reflection are consistent with the formation of a SmA liquid crystalline phase. See L. Jongen et al., *Liq. Cryst.* 28, 1727 (2001).

The presence of the solid intermediate (rotator) phase seen in the SmC$_{10}$ NPs DSC trace is confirmed by the diffraction patterns collected at 80 and 120° C. (FIG. 15C). The low-angle region peaks in the 80° C. pattern are shifted to higher angles, representing a loss of some ordering in the alkyl chains, but the shape and intensity are maintained and

TABLE 3

Summary of DSC data for LnC$_{10}$ NPs, including phase temperature ranges, transition temperatures, and transition enthalpy values (ΔH). In addition to the transitions from crystalline solid to Smectic A mesophase (Cr → SmA) and mesophase to isotropic liquid (SmA → IL), the heavier lanthanides (Sm, Gd, Er) underwent the transition from crystalline solid to a solid intermediate phase (Cr → SI) before forming the SmA mesophase (SI → SmA).

Summary of phase transition temperature and enthalpy for LnC$_{10}$ NPs

| | Mesophase or Intermediate Formation | | | | Intermediate to Mesophase Transition | | Formation of Isotropic Liquid | |
|---|---|---|---|---|---|---|---|---|
| | Cr → SmA | | Cr → SI | | SI → SmA | | SmA → IL | |
| Ln$^{3+}$ | T(° C) | ΔH (kJ mol$^{-1}$) | T(° C) | ΔH (kJ mol$^{-1}$) | T (° C) | ΔH (kJ mol$^{-1}$) | T (° C) | ΔH (kJ mol$^{-1}$) |
| Pr | 88 | 77.99 | — | — | — | — | 130 | 0.85 |
| Nd | 89 | 100.16 | — | — | — | — | 147 | 1.57 |
| Sm | — | — | 78 | 29.28 | 105 | 49.36 | 134 | 2.65 |
| Gd | — | — | 96 | 36.64 | 116 | 22.68 | 137 | 0.73 |
| Er | — | — | 76 | 33.38 | 104 | 105.73 | 133 | 4.73 |

High-Temperature Powder X-Ray Diffraction

Further examination of the behavior of LnC$_{10}$ NPs mesophases was conducted via high-temperature powder X-ray diffraction (HT-PXRD). The lack of reliable PLM data for lanthanide alkanoates leaves HT-PXRD as the only characterization method that can be used to unambiguously determine mesophase identity. See L. Jongen et al., *Liq. Cryst.* 28, 1727 (2001); and Y. Kitagawa et al., *Inorg. Chem.* 59, 5865 (2020). FIGS. 15A-E show a comparison of the PXRD patterns between the solid crystalline room temperature phase and the mesophases that form at elevated temperatures. The LnC$_{10}$ NPs HT-PXRD data support the phase transition temperatures observed in DSC, and the mesophase diffraction patterns were in good agreement with references. See K. Binnemans et al., *Eur. J. Inorg. Chem.*, 1429 (2000); H. Li et al., *J. Phys. Chem. B* 109, 21669 (2005); and L. Jongen et al., *Liq. Cryst.* 28, 1727 (2001).

Transitions associated with mesophase formation were observed in the HT-PXRD patterns as significant shifts in peak position and intensity at temperatures corresponding to the phase transitions observed in DSC traces. Lanthanide alkanoate mesophases retain the lamellar bilayer structure of the solid crystalline state but lose the highly ordered all-trans no reflections are absent. In contrast, the 120° C. pattern displays the characteristics of an SmA liquid crystalline phase.

Two distinct mesophases were also observed in the HT-PXRD patterns of the ErC$_{10}$ NPs (FIG. 15E) but indicate unique behavior by the smallest lanthanide of the series. The 80° C. pattern retains a sharp peak corresponding to the first reflection recorded at room temperature, but also displays a higher intensity peak with a decreased d-spacing value. This peak can still be observed with lower intensity in the 120° C. pattern, coexisting with the SmA phase observed for the other LnC$_{10}$ NPs. This indicates the formation of an additional, unknown LC phase by the ErC$_{10}$ NPs.

LC phases can be identified by the response of their d-spacing values to increasing temperatures, which reflect conformational changes and defect formation in the alkyl chains. Observed values for $d_{max}$ vs. temperature for PrC$_{10}$ and ErC$_{10}$ NPs are plotted in FIG. 15. For both materials, the presence of a SmA LC phase was indicated by the significant decrease in $d_{max}$ values above the melting point compared to the solid crystalline phase. This decrease is due to the "folding" of the organic layer to generate the SmA phase, which occurs via formation of gauche defects in the melting alkyl chains and reduces the separation between the inorganic layers. See F. J. Martinez-Casado et al., *J. Therm. Anal. Calorim.* 108, 399 (2012). In contrast, defect formation via "tilting" processes leads to the formation of a Smectic C (SmC) phase, which displays increased $d_{max}$ values at temperatures above the melting point. This is consistent with the thermal behavior of the unknown LC phase observed for $ErC_{10}$, which showed an expansion of $d_{max}$ values above 70° C. (FIG. 15B). The phase was thus identified as liquid crystalline SmC phase. The appearance of the SmC phase only in the smallest observed $Ln^{3+}$ may be related to steric factors, which suppress certain types of defect formation during the stepwise melting process. See F. J. Martinez-Casado et al., *J. Therm. Anal. Calorim.* 108, 399 (2012).

In summary, HT-PXRD data supported DSC observations of the onset, peak, and temperature range for each phase and transition. Distinct behavioral differences between the larger ($PrC_{10}$, $NdC_{10}$) and smaller ($SmC_{10}$, $GdC_{10}$, $ErC_{10}$) lanthanide alkanoate NPs were observed, with trends matching those seen in DSC. HT-PXRD analysis confirmed the formation of a SmA LC phase by all samples, while the smaller $Ln^{3+}$ also formed a secondary SmC phase alongside the SmA.

Analysis of Liquid Crystalline Behavior in $LnC_{10}$ NPs $LnC_{10}$ NPs offer a unique perspective from which to study the liquid crystalline behavior of these materials. The formation of LC phases by lanthanide alkanoates is enabled by the ability of the long decanoate alkyl chains maintain their integral layered structure even on heating. See H. Li et al., *J. Phys. Chem. B* 109, 21669 (2005). The formation and stability of these thermotropic LC phases depend directly on the anisotropic distribution of electric charge in the COO— anions, and the ability of the interlayer alkyl chains to maintain sufficient distance between the charged layers as the material is heated. See F. J. Martinez-Casado et al., *J. Therm. Anal. Calorim.* 108, 399 (2012). All LC phase transitions involve a loss in short-range order; this occurs in $LnC_{10}$ NPs as increasing temperatures cause the alkyl chains to form gauche defects and eventually lose their all-trans conformation. In contrast, stable alkanoate LC phases must preserve their long-range order by ensuring that the attraction between the charged organic and inorganic layers remains energetically favorable. Instability from the alkyl chain movement causes an increase in electrostatic repulsion between their COO⁻ anions. If the alkyl chains cannot sufficiently resist loss of short-range order and are unable to maintain the interlayer distance, the COO⁻ repulsive forces overcome the stabilizing attractive force. This results in the collapse of the bilayer structure, and the material loses all long-range order as it melts into an ionic liquid phase.

The phase transition behavior of the $LnC_{10}$ NPs illustrates the effect of lanthanide contraction on LC formation and stability. The ability to maintain favorable electrostatic interactions for LC formation is directly related to the $Ln^{3+}$ ionic radius and its impact on the $LnC_{10}$ unit cell. Table 2 shows that $LnC_{10}$ NPs with smaller $Ln^{3+}$ ionic radii have reduced interlayer d-spacing $d_{max}$, which means that the charged organic and inorganic layers experience less separation in the crystalline solid. The resulting steric hindrance forces closer interaction between the COO⁻ anions during heating, increasing the destructive repulsive force. The reduced thermal stability of decanoates with smaller $d_{max}$ values can be observed in bulk materials as lower melting points and the inability to form LC phases when the $Ln^{3+}$ radius<1.175 Å ($Nd^{3+}$). See E. F. Marques et al., *J. Chem. Soc., Faraday Trans.* 94, 1729 (1998); and H. Li et al, *J. Phys. Chem. B* 109, 21669 (2005).

As indicated by the successful formation of LC phases by smaller $Ln^{3+}$ (Sm, Gd, Er), nanoscale $LnC_{10}$ materials seem to have unique thermal stability compared to their bulk counterparts. While lanthanide contraction does not prevent the formation of LC phases by the smaller $LnC_{10}$ NPs, its effects are seen on the formation temperatures, enthalpies, and phase progressions of the SmA phases in each material. One of the most notable effects was the formation of the solid intermediate (SI) or "rotator" phase by the NPs with smaller $Ln^{3+}$ radii. The SI phase forms when alkyl chains become partially molten and begin to develop gauche defects. See K. Binnemans et al., *Inorg. Chem.* 39, 5938 (2000). $LnC_{10}$ SI phases are associated with smaller $Ln^{3+}$ because steric hindrance in their smaller unit cells forces the melting alkyl chains to move by rotating around their axis. As the temperature continues to increase, the alkyl chains become fully molten and enable the formation of the liquid crystalline SmA phase.

The present invention has been described as the solvothermal synthesis of metal alkanoate and metal oxide nanoparticles. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A solvothermal method to synthesize metal alkanoate nanoparticles, comprising the steps of:
   dissolving a metal nitrate precursor in water to provide an aqueous precursor solution,
   dissolving an alkanoic acid in an alcohol to provide an alkanoate solution,
   mixing the aqueous metal precursor solution with the alkanoate solution to provide a mixed solution,
   heating the mixed solution by microwave irradiation to a reaction temperature to form a metal alkanoate precipitate in a solvent,
   isolating the metal alkanoate precipitate from the solvent, and
   washing the metal alkanoate precipitate to provide a powder comprising metal alkanoate nanoparticles.

2. The method of claim 1, wherein the metal comprises a lanthanide.

3. The method of claim 2, wherein the lanthanide comprises La, Ce, Pr, Nd, Sm, Eu, Gd, Tb, Dy, Ho, Er, Tm, or Yb.

4. The method of claim 1, wherein the metal comprises a transition metal.

5. The method of claim 4, wherein the transition metal comprises Ag, Co, Cu, or Pb.

6. The method of claim 1, wherein the alkanoic acid comprises decanoic acid and the metal alkanoate comprises lanthanide decanoate.

7. The method of claim 1, wherein the alcohol comprises a short-chain alcohol.

8. The method of claim 7, wherein the short-chain alcohol comprises methanol, ethanol, propanol, or butanol.

9. The method of claim 1, wherein the reaction temperature is greater than 80° C.

10. The method of claim 1, wherein the metal alkanoate comprises a di- or tri-valent metal cation coordinated to the carboxy group of an alkanoate anion with 4 to 22 carbon atoms in the alkyl chain.

11. The method of claim 1, further comprising calcining the metal alkanoate nanoparticles at a calcination temperature to provide metal oxide nanoparticles.

12. The method of claim 11, wherein the calcination temperature is greater than 400° C.

13. The method of claim 11, wherein the metal alkanoate nanoparticles comprise lanthanide alkanoate nanoparticles and the metal oxide nanoparticles comprise lanthanide oxide nanoparticles.

* * * * *